(12) United States Patent
Itkowitz

(10) Patent No.: US 8,521,331 B2
(45) Date of Patent: Aug. 27, 2013

(54) PATIENT-SIDE SURGEON INTERFACE FOR A MINIMALLY INVASIVE, TELEOPERATED SURGICAL INSTRUMENT

(75) Inventor: Brandon Itkowitz, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 784 days.

(21) Appl. No.: 12/617,937

(22) Filed: Nov. 13, 2009

(65) Prior Publication Data

US 2011/0118748 A1    May 19, 2011

(51) Int. Cl.
| | | |
|---|---|---|
| A61B 19/00 | (2006.01) |
| A61B 17/00 | (2006.01) |
| G05B 15/00 | (2006.01) |
| G06F 19/00 | (2011.01) |

(52) U.S. Cl.
USPC .............. 700/264; 606/1; 606/130; 700/245

(58) Field of Classification Search
USPC .............. 701/245, 450, 257, 258, 259, 264; 606/130, 102, 111, 587; 318/628; 348/51, 348/45; 901/15, 16
See application file for complete search history.

(56) References Cited

U.S. PATENT DOCUMENTS

| | | | | |
|---|---|---|---|---|
| 4,988,981 A | * | 1/1991 | Zimmerman et al. | 345/158 |
| 6,110,130 A | | 8/2000 | Kramer | |
| 6,565,554 B1 | | 5/2003 | Niemeyer | |
| 7,461,423 B2 | * | 12/2008 | Rutherford et al. | 5/646 |
| 7,843,158 B2 | | 11/2010 | Prisco | |
| 2003/0210258 A1 | * | 11/2003 | Williams | 345/700 |
| 2004/0087989 A1 | * | 5/2004 | Brenneman et al. | 606/167 |
| 2006/0235436 A1 | * | 10/2006 | Anderson et al. | 606/130 |
| 2008/0177284 A1 | * | 7/2008 | Lee et al. | 606/130 |
| 2009/0036902 A1 | * | 2/2009 | DiMaio et al. | 606/130 |
| 2009/0177452 A1 | * | 7/2009 | Ullrich et al. | 703/11 |
| 2009/0192523 A1 | * | 7/2009 | Larkin et al. | 606/130 |
| 2009/0268010 A1 | * | 10/2009 | Zhao et al. | 348/45 |

(Continued)

FOREIGN PATENT DOCUMENTS

| | | | |
|---|---|---|---|
| WO | WO0051486 A1 | | 9/2000 |
| WO | WO 0051486 A1 | * | 9/2000 |
| WO | WO2008133956 A2 | | 11/2008 |
| WO | WO 2008133956 A2 | * | 11/2008 |

OTHER PUBLICATIONS

Canesta, Inc., "Canesta 101: Introduction to 3D Vision in CMOS", Whitepaper, Mar. 2008, 20 pages, Internet: http://www.canesta.com/assets/pdf/technicalpapers/Canesta101.pdf.

(Continued)

Primary Examiner — Khoi Tran
Assistant Examiner — Robert Nguyen

(57) ABSTRACT

A patient-side surgeon interface provides enhanced capabilities in using a minimally invasive, teleoperated surgical system. The patient-side surgeon interface has components within the sterile surgical field of the surgery. The components allow a surgeon to control teleoperated slave surgical instruments from within the sterile surgical field. The patient-side surgeon interface permits a surgeon to be in the sterile surgical field adjacent a patient undergoing surgery. Controlling minimally invasive slave surgical instruments from within the sterile surgical field permits minimally invasive surgery combined with direct visualization by the surgeon. The proximity to the patient allows the surgeon to control a teleoperated slave surgical instrument in tandem with controlling manually controlled instruments such as a laparoscopic instrument. Also, the surgeon, from within the sterile surgical field, can use the patient-side surgeon interface to control at least one proxy visual in proctoring another surgeon.

25 Claims, 15 Drawing Sheets

(56) References Cited

U.S. PATENT DOCUMENTS

| | | |
|---|---|---|
| 2010/0013910 A1 | 1/2010 | Farr |
| 2010/0063630 A1* | 3/2010 | Sutherland et al. ............ 700/264 |
| 2010/0082368 A1* | 4/2010 | Gecelter et al. .................... 705/3 |

OTHER PUBLICATIONS

Gokturk, S. et al., "3D Vision Enables Everyday Devices to 'See'", Whitepaper, Apr. 2008, 10 pages, Canesta, Inc., Internet: http://www.canesta.com/assets/pdf/technicalpapers/Why3d.pdf.

"3D Guidance trakSTAR™ Wide-Range", 2009, pp. 1-2 [online], Ascension Technology Corporation, Burlington, VT, USA. Retrieved on Jul. 9, 2010, from the Internet: <URL:http://www.ascension-tech.com/ medical/pdf/TrakStarWRTSpecSheet.pdf>. No author provided.

"3D Technological Principles", pp. 1-5 [online], Hyundai IT Corp. Retrieved on Jul. 9, 2010, from the Internet: <URL:http://www.abs-tech.com/admin/modulos/produtos/upload/mais_informacoes/542/489.pdf>. No author provided.

"Intuitive Surgical Inc.", Jul. 2005, pp. 1-5, Spelman Financial, Ltd., New York, NY, USA. No author provided.

"Stereoscopic Viewing and Displays", pp. 1-2 [online], Pavonine Korea, Inc. Retrieved on Jul. 9, 2010 from the Internet: <URL:http://www.miracube.net/technology/index.php>. No author provided.

Vertut, Jean and Philippe Coiffet, *Teleoperation and Robotics: Evolution and Development*, 1986, 332 pages, English translation: Prentice-Hall, Inc., Inglewood Cliffs, NJ, USA.

U.S. Appl. No. 61/082,432, filed Jul. 21, 2008; Mina Farr et al.

PCT/US10/56345 International Search Report and Written Opinion of the International Searching Authority, mailed Feb. 8, 2011, 15 pages.

\* cited by examiner

PATIENT-SIDE SURGEON INTERFACE FOR A MINIMALLY INVASIVE, TELEOPERATED SURGICAL INSTRUMENT

BACKGROUND

1. Field of Invention

Aspects of this invention are related to minimally invasive, teleoperated surgical systems, and more particularly are related to patient-side surgeon interfaces for minimally invasive, teleoperated surgical systems.

2. Related Art

The da Vinci® Surgical System, manufactured by Intuitive Surgical, Inc., Sunnyvale, Calif., is a minimally invasive, teleoperated robotic surgical system that offers patients many benefits, such as reduced trauma to the body, faster recovery and shorter hospital stay. The da Vinci® Surgical System provides intuitive and ergonomic control of minimally invasive slave surgical instruments, which provides telepresence for the surgeon. This system incorporates a dedicated surgeon console, which provides a three-dimensional stereo viewer, two master tool manipulators, foot pedals for controlling modes of operation, and an ergonomic head and arm rest for prolonged seated use.

While using such a teleoperated robotic surgical system, the surgeon is typically physically separated from the sterile surgical field. Thus, the surgeon relies on assistants in the operating room to perform some tasks at the patient side, which can not be robotically controlled.

SUMMARY

A patient-side surgeon interface provides enhanced capabilities in using a minimally invasive, teleoperated surgical system. The patient-side surgeon interface has at least one component within the sterile surgical field of the surgery. The component allows a surgeon to control at least one teleoperated slave surgical instrument, sometimes referred to as a slave surgical instrument, from within the sterile surgical field. Thus, the patient-side surgeon interface permits a surgeon to be in the sterile surgical field adjacent a patient undergoing surgery.

Controlling minimally invasive slave surgical instruments from within the sterile surgical field permits minimally invasive surgery combined with direct visualization by the surgeon. The proximity to the patient allows the surgeon to control a teleoperated slave surgical instrument together with one or more manually operated instruments such as a laparoscopic instrument. Also, the surgeon, from within the sterile surgical field, can use the patient-side surgeon interface to control a surgical instrument, and/or at least one proxy visual in proctoring another surgeon.

Hence, in one aspect, a minimally invasive surgical system includes a patient-side surgeon interface. The patient-side surgeon interface includes a display device mounted in an operating room and a master interface.

The master interface includes a master tool grip mechanically ungrounded with respect to any object in the operating room. The master interface also includes a hand-tracking transmitter separated and removed from the master tool grip. The hand-tracking transmitter is coupled to the master tool grip by a three-dimensional position tracking technology to generated sensed position and sensed orientation of the master tool grip.

The minimally invasive surgical system also includes a teleoperated slave surgical instrument and a control system coupled to the hand-tracking sensor, to the display device, and to the teleoperated slave surgical instrument. The control system sends control commands to the teleoperated slave surgical instrument in response to sensed information. The control system also updates an image generated by the display device as the teleoperated slave surgical instrument moves in response to the control commands.

In one aspect, the patient-side surgeon interface also includes a stereoscopic image viewer. Upon viewing the image on the display device through the stereoscopic image viewer, a stereoscopic image is seen.

In another aspect, the patient-side surgeon interface also includes a movable stabilization platform. The stabilization platform supports a surgeon's forearms while the surgeon grasps the master tool grip. The stabilization platform can be moved independent from any movement of the display device. In one aspect, the movable stabilization platform includes a plurality of wheels used to move the movable stabilization platform with respect to a position of an operating table. In another aspect, the movable stabilization platform is mounted to an operating table. In yet another aspect, the stabilization platform is mounted to an adjustable mechanical arm with brakes such that the forearm support can be adjusted and used while seated or standing.

In still yet another aspect, the minimally invasive surgical system also includes a surgeon's console, coupled to the control system, including a stereoscope display device and a powered master interface. The control system further comprises a proxy visual module coupled to the stereoscopic display device of the surgeon's console to provide a proxy visual, and coupled to the hand tracking sensor to receive the sensed information characterizing the movement of the master tool grip. Execution of the proxy visual module moves the proxy visual in response to the sensed information.

In one aspect, sensed position and orientation information is generated by moving a mechanically ungrounded master tool grip located in a sterile surgical field. The sensed position and orientation information is in a reference frame associated with a person working within the sterile surgical field, and operating the mechanically ungrounded master tool grip. In one aspect, the reference frame is a body-centric reference frame. Movement of an end effector of a minimally invasive, teleoperated slave surgical instrument is controlled based on the sensed position and orientation information. The end effector is also in the sterile surgical field. Further, a manually operated surgical instrument is controlled by the person using a control handle of the manually operated surgical instrument. The control handle is within the sterile surgical field.

In another aspect, position and orientation of a mechanically ungrounded master tool grip is sensed in a reference frame associated with a person operating the mechanically ungrounded master tool grip. In one aspect, the reference frame is a body-centric reference frame. The position and orientation is sensed when the mechanically ungrounded master tool grip is moved in a field from a hand-tracking transmitter, and is moved within a sterile surgical field.

The sensed position and orientation is received by a control system. The control system generates a control command, using the sensed position and orientation, with respect to a reference frame associated with an image displayed on a display device. The control system sends the control command to a teleoperated slave surgical instrument.

Figure 1A:
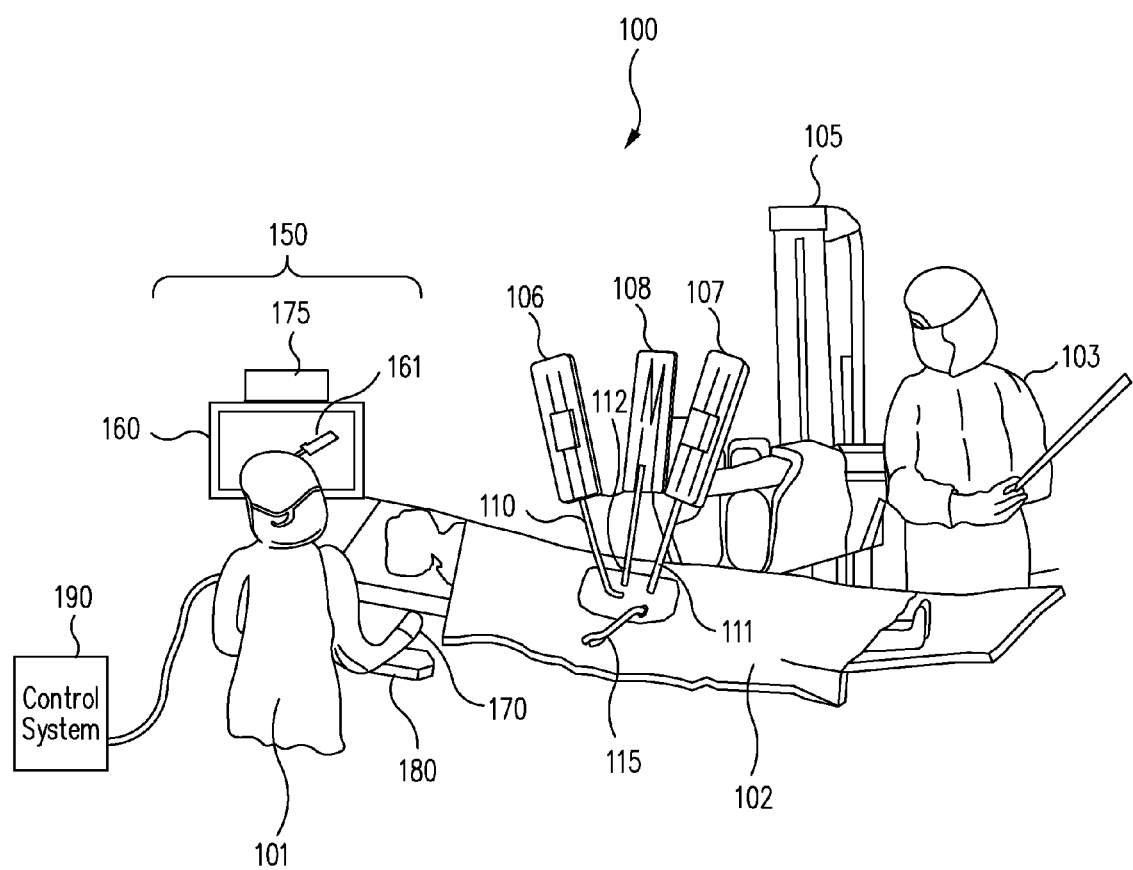
FIG. 1A is a diagrammatic view of a minimally invasive surgical system, which includes a patient-side surgeon interface.

In the drawings, the first digit of a figure number indicates the figure in which the element with that figure number first appeared.

As used herein, a sterile surgical field means an area immediately around a patient that has been prepared for a surgical procedure. The sterile surgical field includes the scrubbed team members, who are properly attired, and all furniture and fixtures in the area.

As used herein, mechanically ungrounded master tool grip means a master tool grip that is unconstrained with respect to possible position and orientation motion in a large working volume. For the purpose of this definition, a large working volume is a volume that permits tracking of position motions within arm's length of the user and tracking all orientations.

DETAILED DESCRIPTION

Figure 1B:
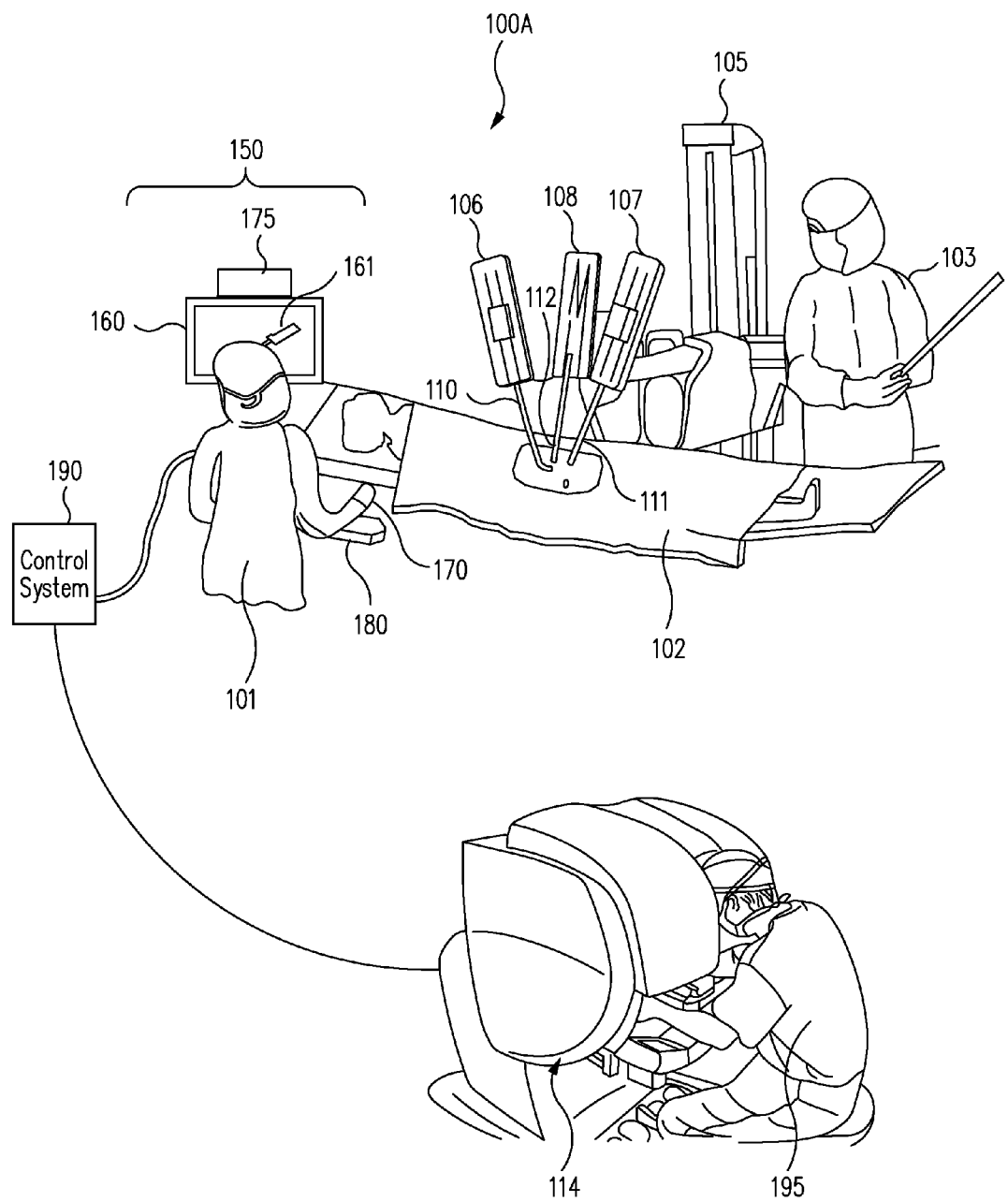
FIG. 1B is a diagrammatic view of a minimally invasive surgical system, which includes a patient-side surgeon interface and a surgeon's console.

Referring in general to FIGS. 1A and 1B, aspects of this invention include a patient-side surgeon interface 150 that provides enhanced capabilities in using minimally invasive, teleoperated surgical system 100. Unlike conventional minimally invasive, teleoperated surgical systems, patient-side surgeon interface 150 has at least one component within the sterile surgical field of the surgery. This component in combination with an image on display device 160 allows a surgeon 101 to control teleoperated slave surgical instruments 110, 111 from within the sterile surgical field. Thus, patient-side surgeon interface 150 permits a surgeon 101 to work within the sterile surgical field adjacent a patient 102 undergoing surgery.

Controlling minimally invasive slave surgical instruments 110, 111 from within the sterile surgical field permits minimally invasive surgery combined with direct visualization of patient 102, cart 105, any manually operated surgical instruments, other machines and/or instruments being used in the surgery, etc., by surgeon 101. The proximity to patient 102 allows surgeon 101 to control an end effector of teleoperated slave surgical instrument 110 together with one or more manually controlled instruments 115, such as a laparoscopic instrument or a stapler.

Also, as explained more completely below, surgeon 101, from within the sterile surgical field, can control at least one proxy visual to proctor surgeon 195 (FIG. 1B). The proxy visual is visible both in display device 160 and in a display device viewed in a surgeon's console 114, which is located outside the sterile surgical field (FIG. 1B). Using master tool grip 170, surgeon 101 can manipulate the proxy visual to demonstrate control and use of teleoperated slave surgical instruments 110, 111. Alternatively, surgeon 195 can control the proxy visual, using the master tool manipulator on surgeon's console 114, to instruct surgeon 101.

Patient-side surgeon interface 150 reduces operating room floor requirements for the minimally invasive, teleoperated surgical system 100. Patient-side surgeon interface 150 provides a lower-cost alternative to a surgeon's console 114 (FIG. 1B) in a conventional minimally invasive, teleoperated surgical system.

In one aspect, patient-side surgeon interface 150 includes (i) a display device 160, (ii) a master interface that in turn includes at least one mechanically ungrounded unpowered master tool grip 170 and typically two mechanically ungrounded unpowered master tool grips, and a hand-tracking transmitter 175 (iii) a foot tray (See FIG. 4C), and optionally (iv) an ergonomic support 180. As explained more completely below, display device 160 can provide either a two-dimensional image, or a three-dimensional image 161 of, for example, a slave surgical instrument 110 and the surgical site.

In one aspect, display device 160 provides an output that the surgeon perceives as a three-dimensional image that includes an image 161 of an end effector of slave surgical instrument 110 and the surgical site. The end effector is located within the sterile surgical field. The three-dimensional image provides three-dimensional depth cues to permit surgeon 101 to assess relative depths of instruments and patient anatomy. The three-dimensional depth cues, in turn, permit surgeon 101 to use visual feedback to steer the end effector of slave surgical instrument 110 using master tool grip 170 to precisely target features within one millimeter of accuracy.

Display device 160 is mounted so that surgeon 101, from a position that allows work within the sterile surgical field, can position display device 160 for easy and comfortable viewing. However, positioning of display device 160 is typically limited to prevent interference with (i) the ability of surgeon 101 to see patient 102; (ii) performance of patient side maneuvers with master tool grip 170; (iii) manual operation of any other surgical instruments; (iv) viewing other displays, or (v) functionality of other instrumentation used in surgery. Also, movement of display device 160 may be inhibited when following between movement of master tool grip 170 and movement of the slave surgical instrument tip is initiated and when following is in progress.

Surgeon 101 sits or stands comfortably at the side of patient 102 while working in the sterile surgical field and looks at display device 160 during the surgery. Surgeon 101 performs a medical procedure by manipulating at least master tool grip 170 (FIG. 1A). In one aspect, surgeon 101 grasps master tool grip 170 between the thumb and forefinger so that targeting and grasping still involves intuitive pointing and pinching motions. Master tool grip 170 is either sterile or draped so that master tool grip 170 may be safely positioned and used within the sterile surgical field for the surgery. In one aspect, an ergonomic forearm rest 180, which may also be in the sterile surgical field, is provided to support the surgeon's forearms or elbows as surgeon 101 manipulates master tool grip 170 during the surgery.

While working in the sterile surgical field, as the surgeon moves master tool grip 170 in one aspect, sensed spatial information and sensed orientation information is provided to control system 190 based on the movement of master tool grip 170. For example, a hand-tracking transmitter 175 generates a field, for example an electromagnetic field, an optical field (e.g., light beams), etc., and the movement of master tool grip 170 in this field provides sensed spatial position and orientation information in a three-dimensional coordinate system.

As explained more completely below, control system 190 maps the sensed spatial motion data and the sensed orientation data to a common reference frame. Control system 190 processes the mapped data and generates commands to appropriately position an end effector, sometimes referred to as a tip, of teleoperated slave surgical instrument 110 based on the movement of master tool grip 170.

Control system 190 uses a teleoperation servo control system to translate and to transfer the sensed motion of master tool grip 170 to an associated robotic arm through control commands so that surgeon 101 can effectively manipulate the tip of slave surgical instrument 110. Thus, surgeon 101, working in the sterile surgical field, uses a master tool grip 170, which is in the sterile surgical field, to teleoperate an end effector of slave surgical instrument 110.

The number of teleoperated slave surgical tools used at one time, and consequently, the number of robotic arms used in system 100 generally depends on the medical procedure to be performed and the space constraints within the operating room, among other factors. If it is necessary to change one or more of the slave surgical instrument being used during a procedure, an assistant 103 may remove the slave surgical instrument no longer being used from its robot arm and replace that slave surgical instrument with another slave surgical instrument from a tray in the operating room. During surgery, the distal end of at least one robotic slave surgical instrument is positioned within the sterile surgical field.

Although a teleoperated robotic surgical system that provides surgical telepresence offers many advantages over conventional open surgery and manually performed minimally invasive surgery, providing the surgeon the capability to perform such telerobotic surgery while working from within the surgical sterile surgical field offers further benefits. For example, patient-side surgeon interface 150 improves safety by allowing surgeon 101, who is performing the operation, to directly observe patient 102 and robotic patient side cart 105 while manipulating slave surgical instruments 110, 111.

Patient-side surgeon interface 150 also allows a single surgeon 101 to operate in the sterile surgical field and perform procedures, which require coordinated use of manual surgical instruments, such as surgical instrument 115, and one or more teleoperated slave surgical instruments 110, 111. This has advantages over the conventional teleoperated surgical systems in which the surgeon operates remote from the surgical field, and an assistant working within the sterile surgical field typically controls a manually operated minimally invasive surgical instrument, such as a stapler. The remote surgeon must then verbally coordinate with the assistant to properly place the manual instrument and to coordinate actions between the instruments (e.g., use the teleoperated instrument to feed tissue to the manually operated instrument).

As described herein, however, surgical work flow is enhanced because the single surgeon 101 may simultaneously and advantageously use together both slave surgical instrument 110 and a manually operated surgical instrument 115 (e.g., a stapler instrument). For example, manually operated surgical instrument 115 includes a control handle that is located within the sterile surgical field. Surgeon 101 uses the control handle to control manually operated surgical instrument 115.

Interface 150 also permits surgeon 101 to control imaging probes, steerable needles, etc. from both inside and outside the body of patient 102. Thus, interface 150 allows surgeon 101 to self-assist when using manually operated minimally invasive tools. Further, for example, in transoral ear, nose, and throat procedures, interface 150 allows surgeon 101 to self-assist when using traditional open surgery instruments with teleoperated slave surgical instruments 110, 111.

Interface 150 promotes collaborative procedures without requiring additional large stand-alone surgical consoles for teleoperated surgical system 100. Also, assistant 103 may share interface 150 to operate other surgical instruments. In addition, multiple surgeons may collaborate using a common display device 160.

In addition, to the aspects described above, patient side surgeon interface 150 also permits surgeon 101 to mentor or collaborate with surgeon 195 (FIG. 1B) without requiring an additional surgeon console. Surgeon 101 sees the same information on display device 160 that surgeon 195 sees with conventional surgeon's console 114. However, because surgeon 101 is working in the sterile surgical field, surgeon 101 may have access to additional information, such as the patient's apparent overall condition, which is not readily available to surgeon 195.

Since surgeons 101 and 195 view the same information, surgeon 101 can demonstrate proper technique and use of teleoperated slave surgical instruments using interface 150. For example, surgeon 101 may use interface 150 to steer at least one proxy visual to visually indicate where to grab tissue, and to visually indicate in which direction to retract the tissue with an instrument. Likewise, remotely located surgeon 195 may demonstrate techniques, either with the use of real or proxy visuals, to sterile surgical field surgeon 101, who may follow along using either real or proxy visuals. Here, a real visual refers to an image of an end effector of a teleoperated slave surgical instrument.

In addition, two surgeons could view display 160 and each have at least one master tool grip. One surgeon could control a proxy visual, while the other surgeon controls an end effector of a slave surgical instrument.

As indicated above, patient side surgeon interface 150 includes at least a master tool grip and tracking system, a display, and optionally an ergonomic support. Also, various mapping and modifications to the conventional control system are implemented. Each of these aspects is described in more detail below.

Master Interface

Figure 2A:
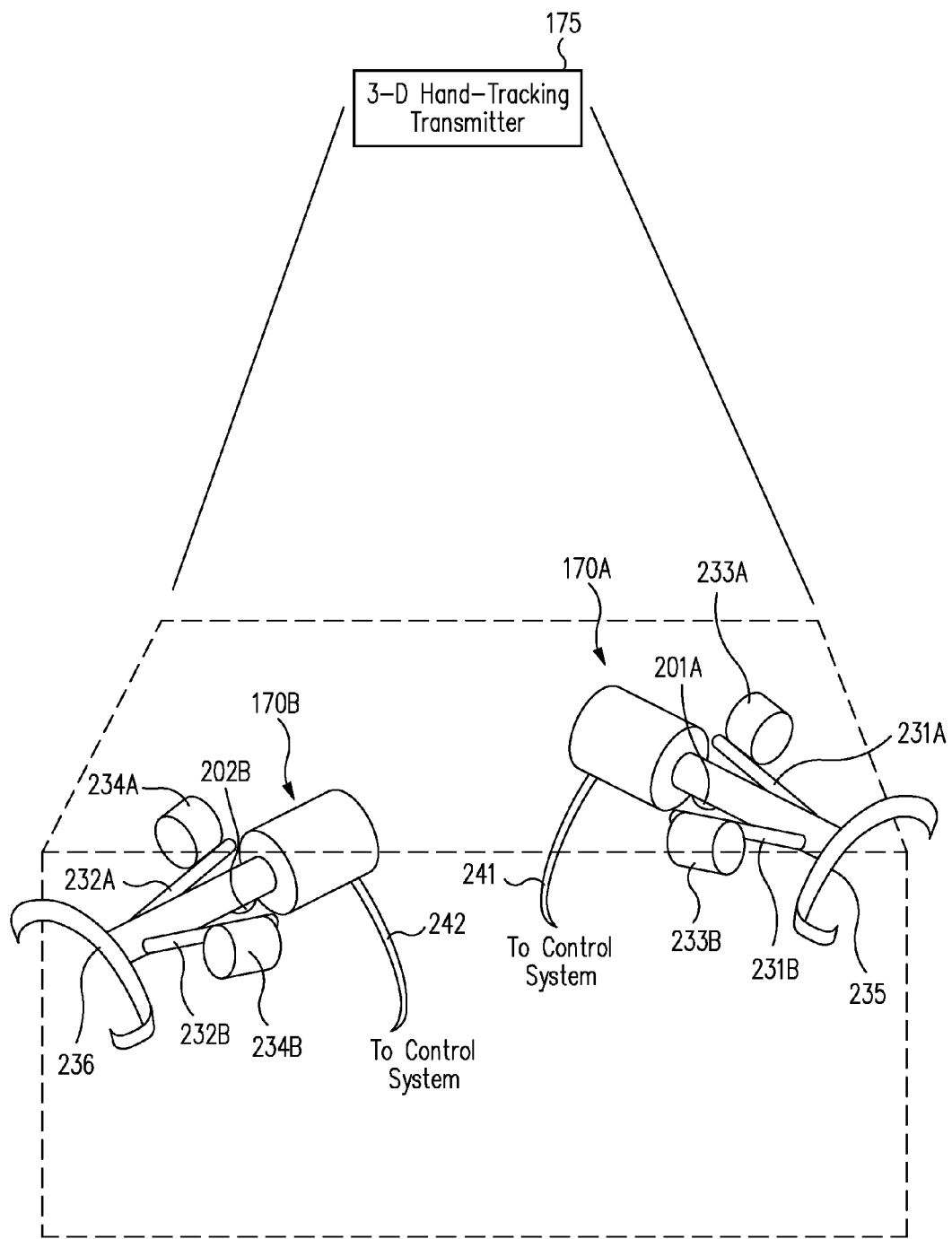
FIG. 2A is a more detailed diagram of one aspect of the master tool grip of FIGS. 1A and 1B.

In this example, as shown in FIG. 2A, patient-side surgeon interface 150 includes a first master tool grip 170A and a second master tool grip 170B. Master tool grips 170A and 170B are illustrative only and are not intended to limit the master tool grips to this specific configuration. In view of this disclosure, a variety of master tool grips can used from within the sterile surgical field to control teleoperated slave surgical instruments, such as instruments 110, 111 (FIGS. 1A and 1B).

The master tool grip technology selected is secured in the hand of surgeon 101. Each master tool grip 170A, 170B also includes presence detection. For example, a capacitance switch, a pressure switch, an infrared beam based presence switch, or some other type of presence detection mechanism is provided to determine whether surgeon 101 is in proper contact with and therefore in control of the master tool grip. This presence detection mechanism is a safety feature that prevents accidental slave tool movement, such as might otherwise occur if the surgeon dropped the master tool grip, handed-off the master tool grip to another surgeon, moved the master tool grip while it is lying on a sterile tray, or took some other action and so no longer has control of the master tool grip.

In one aspect, master tool grip 170A, 170B includes at least one mode control button 201A, 201B. A mode control button 201A, 201B is used in conjunction with at least one of following (which initiates following between motions of a master tool grip and the associated teleoperated slave surgical instrument), master clutch activation (which decouples master control of the slave instrument), endoscopic camera control (which allows the master to control endoscope movement or features, such as focus or electronic zoom), robotic arm swap (which swaps a particular master control between two slave instruments), and tilepro swap, (which toggles the display of auxiliary video windows on the surgeon's display). The number and function of mode control buttons implemented on master tool grips 170A, 170B is complementary to the functionally associated with the foot pedal(s) in the foot tray, described more completely below.

When there are only two master tool grips 170A, 170B in system 100, and when surgeon 101 wants to control movement of a slave surgical instrument other than the two slave surgical instruments coupled to the two master tool grips, surgeon 101 may lock one or both of the two slave surgical instruments in place. Surgeon 101 then associates one or both of the master tool grips with other slave surgical instruments held by other of the robotic arms by tapping the button on the master tool grip, which, in this implementation, provides swap association of the master tool grip to another slave surgical instrument.

In one aspect, each master tool grip 170A, 170B provides a tactile sense of handedness (e.g., particular shapes adapted to either the left or right hand) so that one master tool grip is for the left hand of surgeon 101 and another master tool grip is for the right hand of surgeon 101. In addition, the particular grip style of the master tool grip can be customized to accommodate the preference of the surgeon using the master tool grip.

In the example of FIG. 2A, each master tool grip 170A, 170B includes two levers 231A, 231B, 232A, 232B, each with a finger loop 233A, 233B, 234A, 234B so that surgeon 101 (FIGS. 1A and 1B) typically can grasp the pair of levers between the thumb and forefinger. A palm rest 235, 236 fits in the palm of the surgeon's hand and extends around the palm to the back of the hand, in this example. Other examples of master tool grips include, but are not limited to, a glove device and a thimble device. Also, a master tool grip could be implemented as a pistol grip device or a pencil grip device. See also FIGS. 2B and 2C, which are described below.

Master tool grips 170, 170A, 170B are mechanically ungrounded with respect to all equipment in the operating room. A cable 241, 242 connects master tool grip 170A, 170B to control system 190. In one aspect, cable 241, 242 carries position and orientation information from sensors in master tool grip 170A, 170B to control system 190 as well as sensor data for grip closure and state data for button inputs on master tool grip 170A, 170B.

Use of a cable to transmit sensed position and orientation data to control system 190 is illustrative only and is not intended to be limiting to this specific aspect. In view of this disclosure one knowledgeable in the field can select a mechanism to transmit sensed position and orientation data from the master tool grip or master tool grips to control system 190 (e.g., by use of wireless connection).

Cable 241, 242 does not inhibit motion of master tool grip 170A, 170B. Since each master tool grip 170A, 170B is mechanically ungrounded, each master tool grip is effectively unconstrained for both position and orientation motions within the surgeon's reachable workspace and the hand-tracking transmitter's workspace (e.g., sway, heave, surge, pitch, yaw, and roll in a Cartesian coordinate system). Since each master tool grip 170A, 170B also includes a pincher grip mechanism, each master tool grip 170A, 170B has at least seven degrees of freedom.

Hand-tracking transmitter 175 can be an electromagnetic spatial tracking system, inertial spatial tracking system, optical spatial tracking system, or sonic spatial tracking system, for example. The device that provides the sensed information may vary depending on the particular spatial tracking system or combination of systems used. In each implementation, at least sensed position and orientation information for a master tool grip is provided to the control system.

In some aspects, a combination of an electromagnetic spatial tracking system and an inertial spatial tracking system or a combination of an optical spatial tracking system and an inertial spatial tracking system may be used. The inertial spatial tracking system has a high update frequency and high resolution, but only provides differential tracking information, which is susceptible to absolute position drift when integrated. The differential tracking information from the inertial spatial tracking can be fused with the absolute tracking information from the other spatial tracking system in a complementary fashion to provide drift-free absolute position tracking with high update frequency and high resolution for mechanically ungrounded master tool grips.

In one aspect, irrespective of the particular implementation of the spatial and orientation tracking, the tracking system provides reliable and continuous input data to control system 190. High resolution position and orientation sensing provides at least better than one millimeter position resolution and less than one degree rotation resolution. The data provided to control system 190 has a low latency and high update frequency, for example a latency of at most fifteen milliseconds and update rate of at least forty Hertz.

Figure 2B:
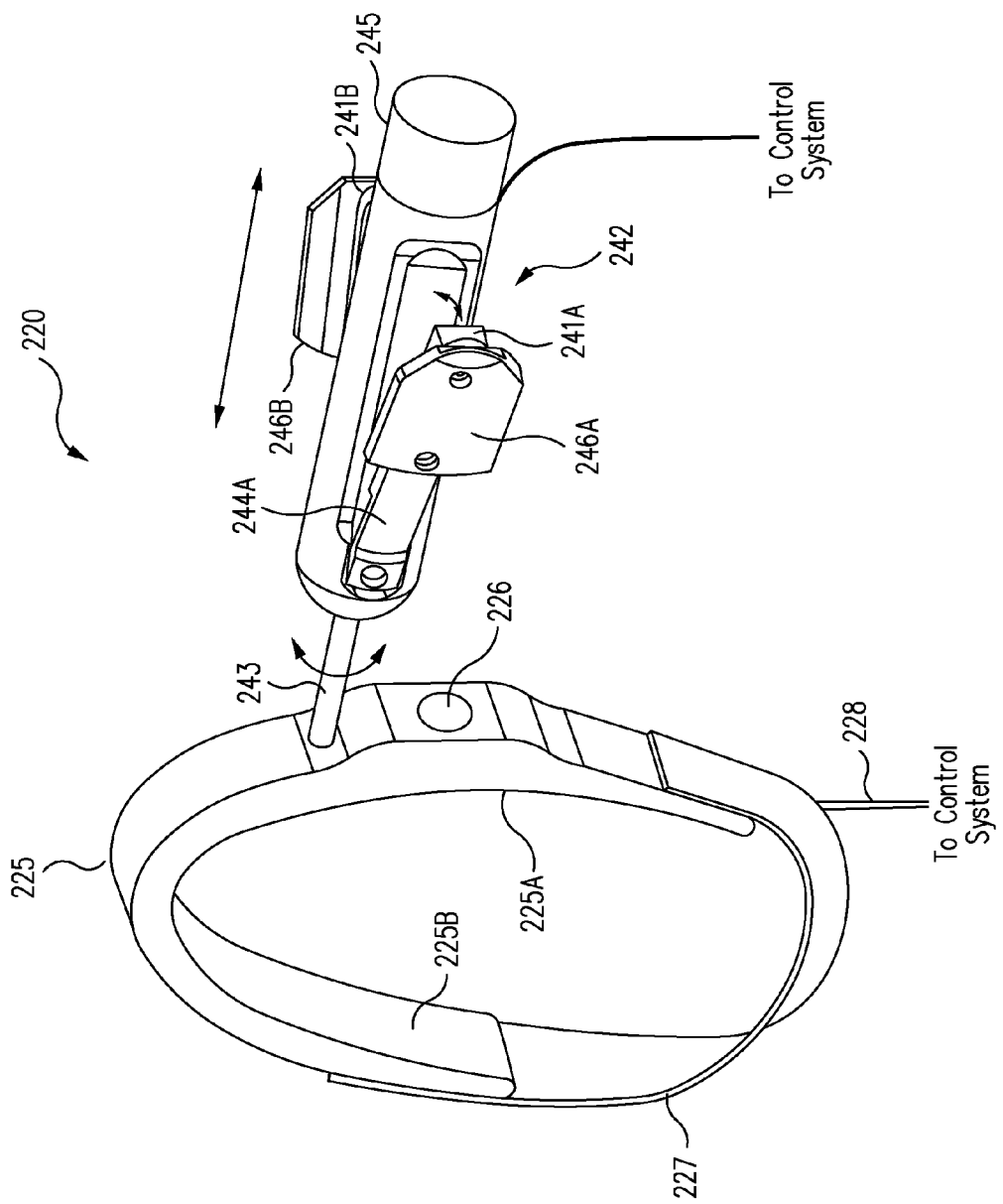
FIG. 2B is a more detailed diagram of another aspect of the master tool grip of FIGS. 1A and 1B.

FIG. 2B illustrates another embodiment of a master tool grip 220. Master tool grip 220 includes a cuff 225 with a strap 227, a shaft 243 and a body 242.

Cuff 225 fits about the hand of surgeon 101 so that inner surface 225B is over back of the hand of the surgeon and opposite inner surface 225A is over the palm of the surgeon. Strap 226, which in one aspect is a Velcro strap, secures cuff 225 to the hand of the surgeon.

Cuff 225 is sized to fit comfortably around the circumference of the surgeon's hand. In one aspect, cuff 225 has a circumference of six inches (15.3 cm) and strap 227 is sized so that cuff 225 can be used on hands with a circumference of about 6.8 to about 9.1 inches (17.3 cm to 23.1 cm).

In one aspect, when strap 226 is in place and secured to both parts of cuff 225, a presence detection switch is activated, but any of the presence detection techniques described above could be used.

A mode control button 226 is positioned on an outer surface of cuff 225. Mode control button 226 is positioned so that when a surgeon is grasping lever 241A and lever 241B between the thumb and forefinger, one of the other fingers of the surgeon can reach and depress mode control button 226.

A body 242 of master tool grip 220 is slideably mounted on a shaft 243. Shaft 243 is affixed to cuff 225. In one aspect, body 242 moves along shaft 243 up to 1.8 inches (4.6 cm) away from cuff 225. Body 242 also rotates about shaft 243.

Two levers 241A, 241B are mounted on body 242 at one end. The configurations of levers 241A, 241B are similar and so only lever 241A is considered in detail.

Lever 241A has a contact plate 246A mounted on an end of the lever opposite the end mounted on body 242. Surgeon 101 (FIGS. 1A and 1B) typically can grasp contact plates 246A and 246B between the thumb and forefinger and depress contact plates 246A and 246B toward body 242 to increase the grasp of the teleoperated slave surgical instrument end effector. Thus, levers 241A, 241B are mounted to body 242 in a way that emulates the grasping, or other operation, of the end effector. For example, variable resistance springs could be used so that as contact plates 246A, 246B get closer to body 242, the resistance to moving contact plates 246A, 246B farther in that direction increases.

Mounted on lever 241, between contact plate 246A and the attachment point to body 242, is a closure sensor 244A that includes a magnet and a Hall Effect sensor. Closure sensor 244A provide grasp closure information as lever 241A moves towards or away from body 242 and control system 190 uses the grasp closure information in controlling the closure of the end effector of the teleoperated slave surgical instrument.

Mounted on the end of body 242 distal to cuff 225 is an electromagnetic sensor 245 that is used in combination with the field from hand tracking transmitter 175 to generate sensed position information and sensed orientation information as master tool tracker 220 moves within the field from hand tracking transmitter 175.

Figure 2C:
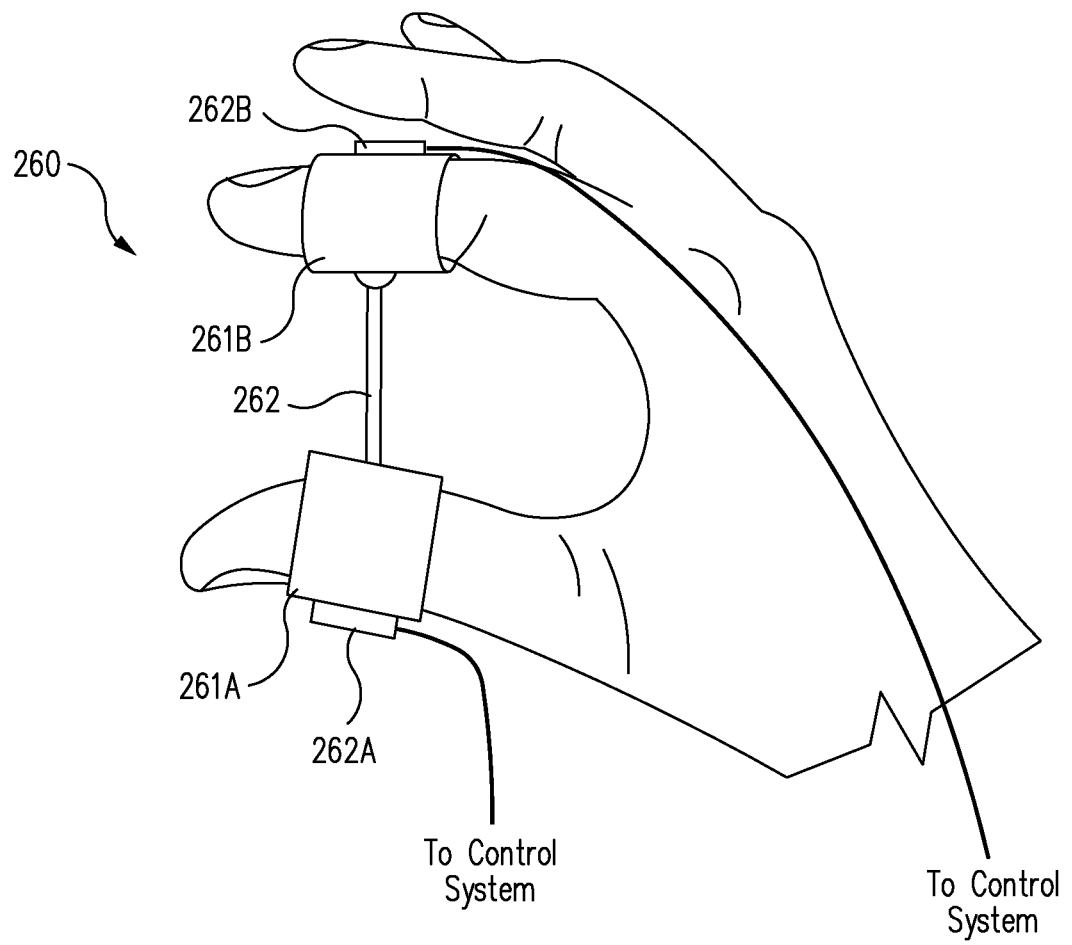
FIG. 2C is a more detailed diagram of yet another aspect of the master tool grip of FIGS. 1A and 1B.

FIG. 2C is an illustration of yet another master tool grip 260. In this embodiment, in place of a glove with instrumented fingers, finger loops 261A, 261B are placed on the thumb and forefinger of the surgeon.

Each finger loop 261A, 261B has a small electromagnetic senor 262A, 262B mounted thereon. A member 262 extends between finger loop 261A and 261B. In one aspect, member 262 emulates the closure of the slave surgical tool end effector and provides grip closure information.

As finger loops 261A, 261B are moved apart, the end effector is opened. As finger loops 261A, 261B are moved towards each other, member 262 provides resistance to simulate the closing and grasping (if appropriate) of the end effector. To actuate the roll axis, surgeon 101 simply rubs the finger and thumb together and the change in orientation of sensors 262A, 2623 relative to one another corresponds to the amount of roll.

The various embodiments described herein of the master tool grip are illustrative only and are not intended to be limiting. In one aspect, each master tool grip includes a secure way to hold the master tool grip in the hand of the surgeon, while accommodating various grip preferences. The master grip allows the surgeon to perform both gross and fine motions easily.

In one aspect, the master tool grip incorporates at least one mode control button. The master tool grip allows a surgeon to remove the finger and the thumb from the master tool grip easily. In one aspect, the master grip incorporates a separately sensed roll axis. The master grip detects the presence of the surgeon and accommodates a three-dimensional tracking sensor. The master tool grip also accommodates a sterile covering when the master grip cannot be sterilized. In some aspects, the master tool grip maintains comparable weight and mass distribution to surgical instruments.

Display Device

Figure 3A:
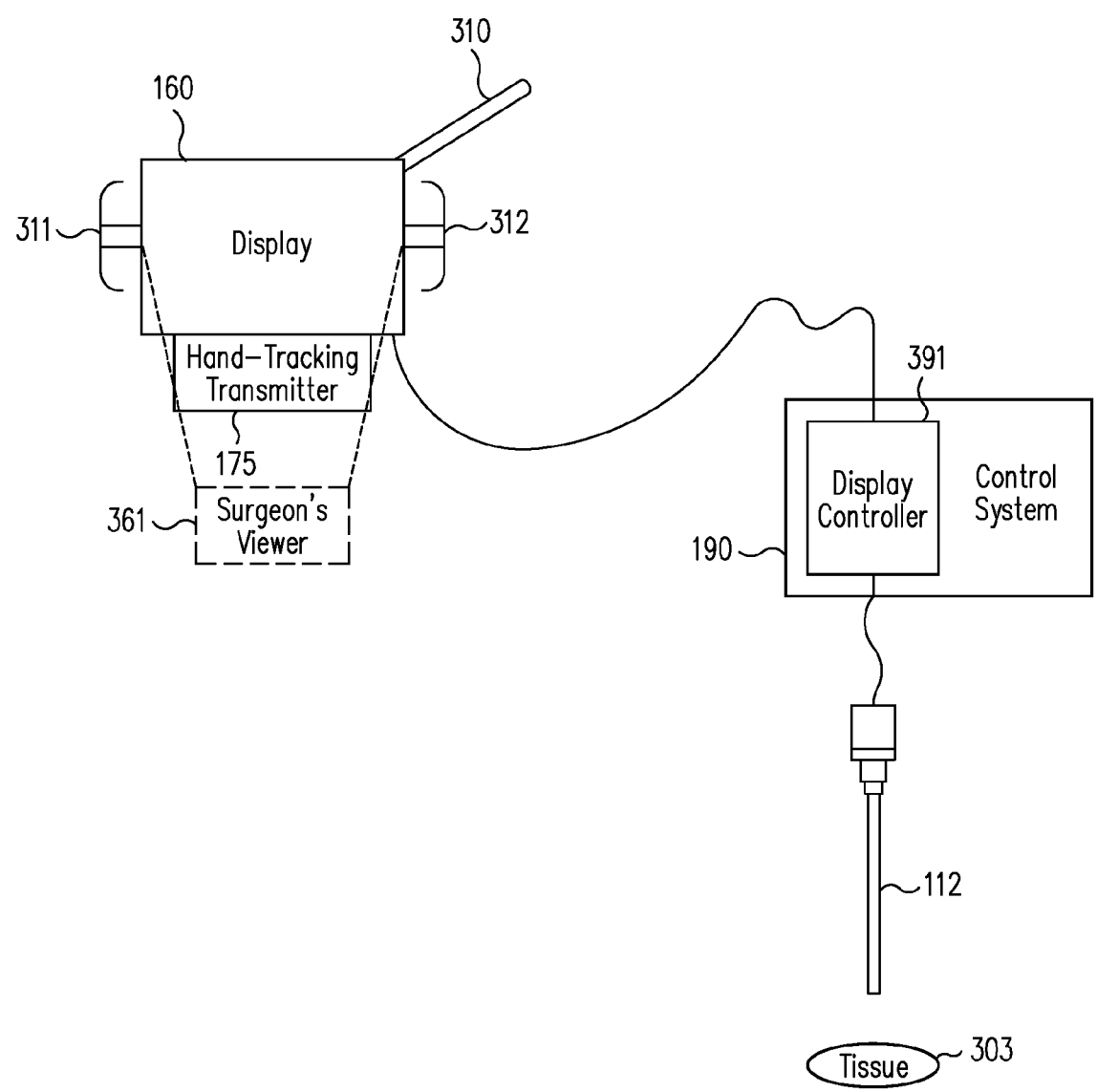
FIG. 3A is a more detailed diagram of one aspect of the display device of FIGS. 1A and 1B.

FIG. 3A is a more detailed block diagram of one aspect of a system that provides an image on display device 160, which is, for example, a liquid crystal display (LCD) device. A conventional stereoscopic endoscope 112 provides left and right channel images of tissue of patient 102 and any end effectors of surgical instruments 110 and 111 in the field of view of stereoscopic endoscope 112.

Stereoscopic endoscope 112 includes two channels for transporting light from tissue (e.g., channels for left and right images). The light transported in each channel represents a different view of the tissue. The light can include one or more images. The light is captured by charge-coupled devices—cameras. The information from the charge-coupled devices is processed by a video controller 391 in control system 190, and appropriate updated information is provided to display device 160 by video controller 391. The particular information provided to display device 160 by video controller 391 depends on the characteristics of display device 160, as discussed more completely below.

As described above, display device 160 can provide images that, in some aspects, may be perceived by surgeon 101 as two-dimensional images and in other aspect, may be perceived by surgeon 101 as three-dimensional images. The ability to see in three-dimensions and perceive relative depths of anatomy and instruments is advantageous compared to typical two-dimensional images provided in conventional manually performed laparoscopic procedures. Accurate stereoscopic depth cues can reduce cognitive load and improve efficiency of motion. However, accurate stereoscopic cues require preservation of eye separation and working distance ratios.

In one aspect, display device 160 is mounted on a boom 310 to allow convenient placement and reorientation of display device 160 with respect to patient 102 and at least surgeon 101. Display device 160 and/or the boom include handles 311, 312 so that display device 160 can be moved, as described above.

In one aspect, handles 311,312 are draped so that handles 311, 312 are included in the sterile surgical field. This permits moving display device 160 by a person working in the sterile surgical field.

Boom 310 includes, in one aspect, brakes so that display device 160 cannot be moved while system 100 is in a mode in which the slave surgical instruments follow movements of the master tool grips (following mode). Alternatively, in one aspect, any movement display device 160, while system 100 is in the following mode, interrupts the following mode. In some cases, master tool grip motion is sensed with respect to the display device 160, so display device 160 is not allowed to move while the system in the following mode. Irrespective of the implementation, in one aspect, display device 160 includes a display motion interlock coupled to control system 190, and this interlock prevents display movement in certain system operating modes in which such movement would be improper and/or disorienting to surgeon 101.

In addition, display device 160 includes a surgeon presence switch. When surgeon 101 is facing display device 160 and is within a range of the surgeon presence switch, the switch provides a signal to control system 190 that allows control system 190 to enter and stay in the following mode. When surgeon 101 is either not facing display device 160 or not within the range of the switch, the surgeon presence switch provides a signal to control system 190 that inhibits control system 190 from being in the following mode. In one aspect, one or more infrared (IR) range sensors are used for sensing close-range distances of surgeon 101 from display 160 or alternatively from surgeon's viewer 361.

The surgeon presence switch is a safety feature that prevents surgeon 101 from operating a slave surgical instrument when surgeon 101 is not in a position to properly evaluate the visual depth cues in the three-dimensional image. The surgeon presence switch is an example of a display-based presence interlock coupled to control system 190.

As indicated above, the information provided to display device 160 by display controller 391 depends upon the type of display utilized. For a three-dimensional image on display device 160, several different implementations can be utilized.

In a first implementation, display device 160 provides a pair of polarized images and surgeon 101 wears special glasses 361. Surgeon 101 sees a three-dimensional image when viewing the pair of polarized images with special glasses 361. The polarized images can be generated in multiple ways. In a first aspect, a display includes features that automatically generate the pair of polarized images. In a second aspect, a film is applied to the screen of a liquid crystal display that generates the pair of polarized images. In both cases, passive glasses with polarized lenses are required to view the three-dimensional image.

In either of these approaches, in one aspect, the polarization of the image on the LCD display is changed on a line-by-line basis. For example, the even numbered lines in the displayed image are polarized in one way and the odd numbered lines in the displayed image are polarized in another way. Typically, the polarization for the even numbered lines is perpendicular to the polarization for the odd numbered lines. The left eye image can be the polarized image from the even numbered lines and, for this example, the right eye image would be the polarized image from the odd numbered lines. This aspect requires that control system 190 provides display device 160 a composite image that contains both left eye and right eye information on a line-by-line basis. This approach requires the use of passive polarized glasses 361.

This approach provides high resolution images and is multi-user capable due to a wide field of view. There is no dependence on refresh rates and no flickering. Also, surgeon 101 is not limited to a specific location, because the display can be viewed at a distance in a range of 0.7 m to 3 m. However, this approach can suffer from ghosting artifacts and distracting distortion from lateral head motion.

An example of a display with the characteristics discussed above is the Miracube G240M provided by Pavonnine Korea, Inc., (406-130) Pavonne R & D Center #7-42, Songdo, Yeonsu-gu, Incheon, Korea. Another example of a display with such characteristics is the GD-463D10 provided by JVC U.S.A., 1700 Valley Road, Wayne, N.J. 07470. In addition, polarizing films with these characteristics are commercially available.

In another implementation, dual images from stereoscopic endoscope 112 can be presented on display device 160 by control system 190, and a stereo viewer 361 is mounted on a boom so that stereo viewer 361 is a fixed distance from display device 160. Stereo viewer 361 includes adjustable mirrors that reflect the stereo-image pair from display device 160 onto eyes of surgeon 101, and in turn the surgeon's brain fuses the images into a single, sharp three-dimensional scene. In one example, stereo viewer 361 is a Wheatstone mirror stereoscope.

Figure 3B:
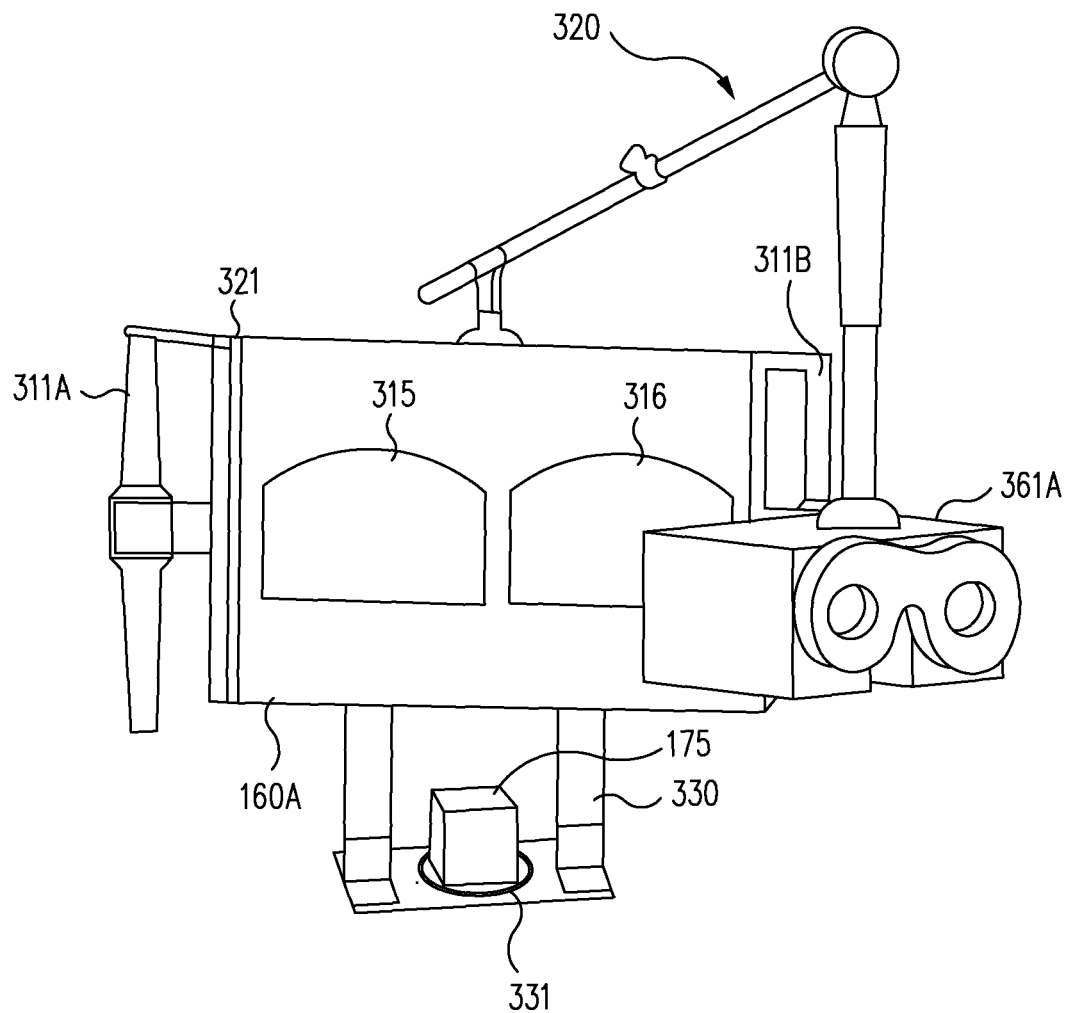
FIG. 3B is a more detailed diagram of another aspect of the display device of FIGS. 1A and 1B.

FIG. 3B is a more detailed illustration of a Wheatstone mirror stereoscope viewer 361A with a display device 160A. In this aspect, display device 160A is mounted in a mounting bracket 321 that provides handles 311A, 311B. Mounting bracket 321, in one aspect, is attacked to boom 310.

Left and right images 315, 316 from stereoscopic endoscope 112 are displayed, by video controller 391, on display device 160A. Viewer 361A is attached to mounting bracket 321 by an extension boom 320. Extension boom 320 allows adjustment of the distance from display device 160A to viewer 361A, and adjustment of the vertical height of viewer 361A. Also, extension boom 320 rotates so that viewer 361A can be rotated out of the way to view display device 160A directly.

In the aspect of FIG. 3B, attached to mounting bracket 321 is a support assembly 330 for hand-tracking transmitter 175. Support assembly 330 includes a turntable 331 on which hand-tracking transmitter 175 is mounted. In one aspect, turntable 331 is implemented as a Lazy Susan apparatus.

Since this implementation of stereo viewer 361, 361A uses mirrors, full color is supported. The three-dimensional image is not haunted by ghost images, and is completely free from screen flicker, which allows for easy viewing. The image provides accurate stereo depth cues. The position of stereo viewer 361, 361A is located at a good viewing distance from the display device. Also, stereo viewer 361 supports a head-in sensor for surgeon presence detection and maintains proper head alignment for motion mapping. The resolution of display device 160 determines the stereo image resolution.

A stereo viewer that is capable of viewing stereo images located directly in front of the viewer is the ScreenScope LCD Adjustable of Berezin Stereo Photography Products, 21686 Abedul, Mission Viejo, Calif. 92691 USA. However, in some aspects, it is advantageous to be able to view stereo images that are collocated with the hand motion workspace. This is achieved by using a mirror assembly like a periscope with such a stereo viewer. The incident mirrors, in the mirror assembly, for the eyes can have a different pitch angle than the mirrors that reflect the images from display device 160. In one aspect, the angle of the incident mirrors for the eyes is adjustable via viewer eye pieces in which these mirrors are mounted. Sixty degrees down from horizontal has been found to be a good working angle for collocation.

The stereo viewer limits the options available to surgeon with respect to selecting a patient side position. However, the stereo viewer facilitates the implementations of the various locks described above and can be mounted on a patient-cart boom to reach many of the working positions desired by surgeon 101. This implementation does not permit multiple users to simultaneously view the same three-dimensional image using display device 160.

In still another aspect, active glasses 361 are used to view an image on display device 160. Active glasses 361 are sometimes referred to as shutter glasses.

Active glasses 361 "turn off" each eye in time with a refresh rate of display device 160. Each lens in active glasses 361 is effectively a one pixel LCD screen that is turned off (black) or on (clear) depending on which eye should see the image displayed on display device 160.

If display device 160 is a 120 Hz LCD device, 120 frames per second of video are displayed so that 60 frames for each eye per second are displayed. This is sometimes referred to as page flipping.

A wireless connection or an infrared connection is used to synchronize active glasses 361 with display device 160. When the left eye frame is shown on display device 160, the left lens is completely open and during the time the screen refreshes with the next frame for the right eye, active glasses 361 must also switch opacity of the lenses. If display device 160 is the 120 Hz LCD device, 120 frames per second of video are displayed so that 60 frames for each eye per second are provided by control system 190. A 120 Hz LCD display that can be used is available from Samsung.

In this aspect, the infrared (IR) shutter signal could be used as the surgeon presence signal. The surgeon must be facing display device 160 for the IR shutter signal emitted by display device 160 to be detected by active shutter glasses 361. This detection could be relayed to the control system to confirm presence as part of the safety interlock. While use of active shutter glasses 361 provides good image quality and a large, immersive display, surgeon 101 must stay within line of sight of display device 160 and avoid lateral head motion to minimize distracting distortion.

In still another aspect, display device 160 is not mounted on a boom and instead is a head mounted display unit. The head mounted display unit includes two small form-factor LCD displays with viewer eye-pieces that display independent images for the left and right eyes. The eye pieces are adjustable for optimal alignment with the user's eye, including adjustment for inter-pupilary distance and gaze direction. The optics within the eye pieces gives the impression that the image is floating in front of the viewer within arm's length. The head mounted display provides accurate stereoscopic depth cues and has a good viewing distance. The head mounted display also supports vision collocation and a head-in sensor as the presence sensor. One head mounted display suitable for use is the 3D-HD Personal Head Display provided by Vision Systems Group, A Division of Viking Systems, 134 Flanders Rd., Westborough, Mass.

Figure 3C:
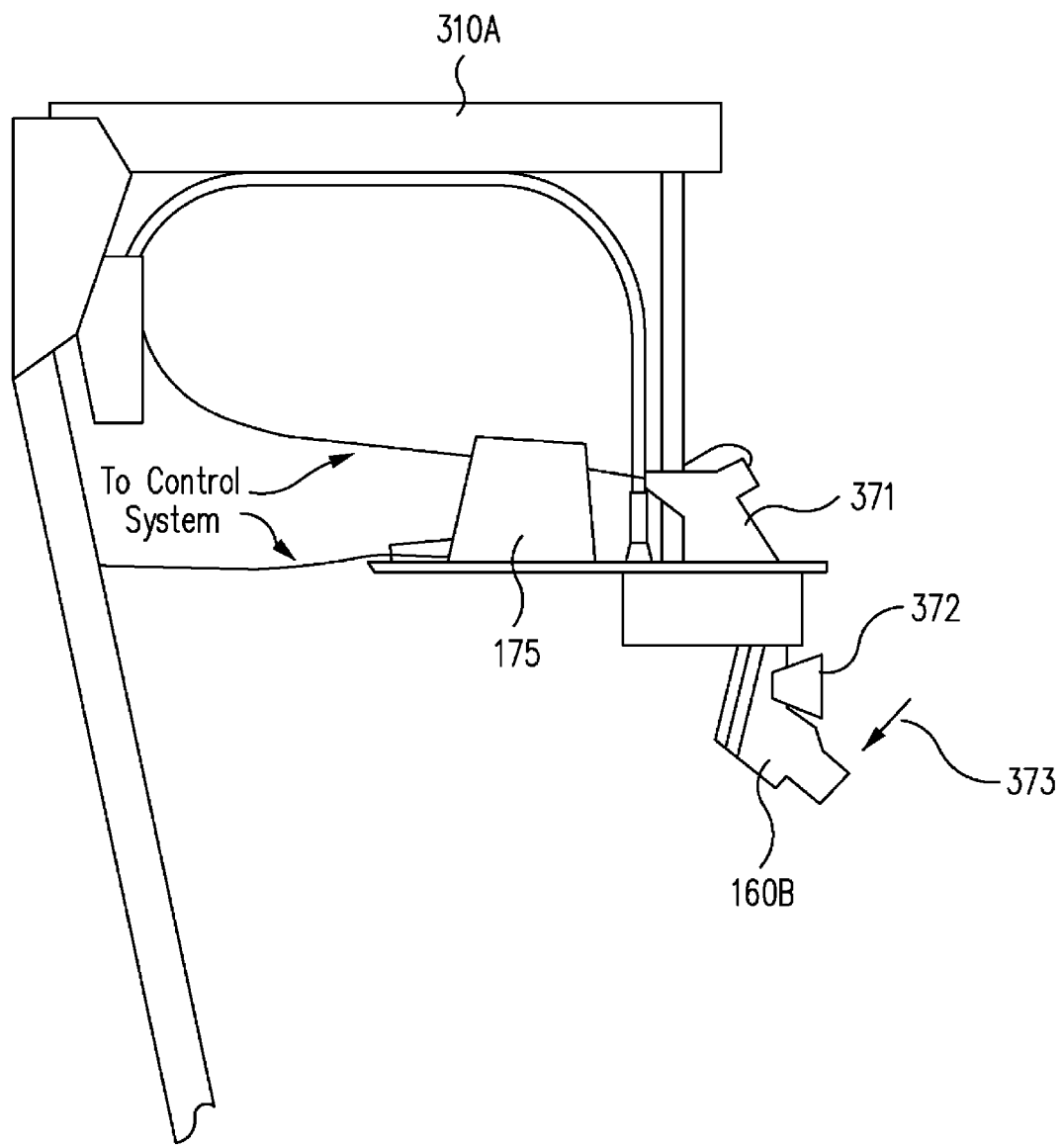
FIG. 3C is a more detailed diagram of yet another aspect of the display device of FIGS. 1A and 1B.

In still another aspect, the head-mounted display technology is also available in a compact boom-mounted display form factor. See FIG. 3C. In this aspect, display device 160B is mounted on a boom 310A that is directly attached to the robotic patient-side cart 305 or a stand-alone cart. This technology supports most of the working positions desired by the surgeon at the patient-side cart, and supports a head-in sensor 371, and a head rest 372. Additionally, the angle of the eye pieces allows for ideal collocation of vision with the hand tracking workspace. Arrow 373 represents the line of sight of the surgeon using display device 160B, which, in one embodiment, is angled downward from the horizontal by sixty degrees. Also, in this aspect, hand-tracking transmitter 175 is supported by boom 310A.

In another aspect, display device 160 is an auto-stereoscopic display, which does not require special glasses or a stereo viewer and so surgeon's viewer 361 is not used. The auto-stereoscopic display delivers separate images to each eye without requiring the use of viewing glasses. There are two main technologies used to generate an auto-stereoscopic display: use of a barrier to block light destined for the contralateral eye, or use of a lenticular lens to direct light into the chosen eye.

A parallax barrier has fine vertical slits in an opaque medium. The barrier is placed in front of an image on display device 160 with left and right images presented in the vertical slits. If the frequency of image slits and barrier slits match and surgeon 101 is a required distance from the barrier, left and right images can be seen by the left eye and the right eye, respectively, of surgeon 101. There is no need for polarized glasses. However, there are a limited number of viewing positions, which in turn results in limited freedom in the choice of patient side positions by surgeon 101.

Mode Control

Patient-side surgeon interface 150 includes an interface for controlling system modes, such as: following mode (slave surgical instruments follow movements of the master tool grips), master clutch mode (disengaging slave actuation from master movement), camera control mode (enabling endoscope movement), energy tools mode (enabling surgical energy tool control (e.g., electrocautery tools), camera focus mode (enabling camera focus control), arm swapping (allowing various master and slave arm control combinations), and tilepro swapping mode (enabling control of various picture displays in the surgeon's display, e.g., swapping between a full screen display and a display in which the surgeon views two or more separate images or data screens). The interface for controlling system modes is readily accessible by surgeon 101 and supports both on/off activation and triggered activation of the various operating modes.

The interface for controlling system modes allows mode control inputs to be mapped and controlled by multiple users in a mutually exclusive fashion. The interface also enables user independent master clutch. In one aspect, the interface is sterilizable. The interface for controlling system modes is easy to learn and to remember. The interface for controlling system modes is configured to minimize unintended mode activations.

The interface for controlling system modes can be alone or in combination one or more buttons, sensors and foot petals. For example, buttons can be included on the master tool grips that when depressed active master clutch and camera control, as described above. A quick tap of the same buttons triggers an arm swap or a tilepro swap. A particular functionality for the normal tap and a particular functionality of the quick tap are assigned to each button.

In one aspect, the interface for controlling system modes includes a foot pedal tray 430 (FIG. 4C) that includes at least one foot pedal 431. In one aspect, foot pedal tray 430 is a small pod that is similar to the right-half of a conventional foot pedal tray for controlling energy activation in a da Vinci® Surgical System Model IS3000 (see U.S. patent application Ser. No. 12/400,726 (filed Mar. 9, 2009), which is incorporated herein by reference). However, in some aspects, the full conventional foot pedal tray may be used.

Ergonomic Support

As illustrated in FIGS. 1A and 1B, patient-side surgeon interface 150 includes a movable ergonomic forearm support 180 that functions as a bench armrest for the forearm(s) or elbow(s) of surgeon 101. Forearm support 180 provides stability for fine motion of master tool grips 170, 170A, 170B. Forearm support 180 also maintains a proprioceptive relationship between the hands for coordinated tasks.

Figure 4A:
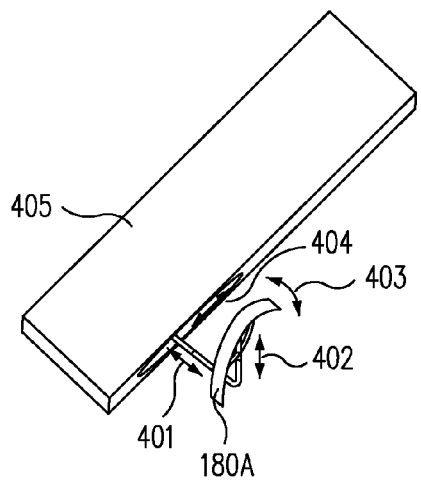
FIGS. 4A and 4B illustrate aspects of the movable ergonomic support of FIGS. 1A and 1B.

In the example of FIG. 4A, forearm/elbow support 180A is attached to operating table 405. As used herein, forearm/elbow support means that support can be provided to either the forearm or the elbow. Forearm/elbow support 180A is movable in multiple dimensions, e.g., along the length of operating table 405 as shown by arrow 404, nearer to and away from operating table as shown by arrow 401, and up and down with respect to the surface of operating table 405 as shown by arrow 402. Also, in this example, forearm/elbow 180A support can pivot about its center as shown by arrow 403. Forearm/elbow support 180A can be used either while surgeon 101 is standing or is seated. Alternatively, forearm/elbow support 180A could be attached to a movable boom with brakes instead of to operating table 405. The movable boom can be adjusted for standing or seated use, and the movable boom structure is strong enough to withstand the force of a surgeon leaning against the boom.

Figure 4B:
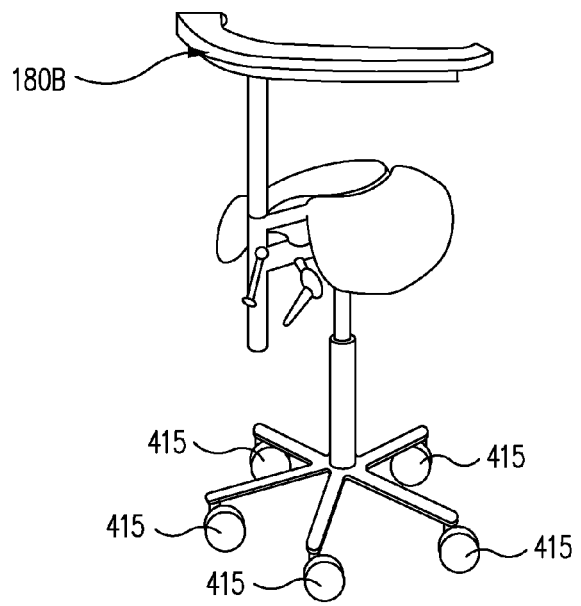
Figure 4C:
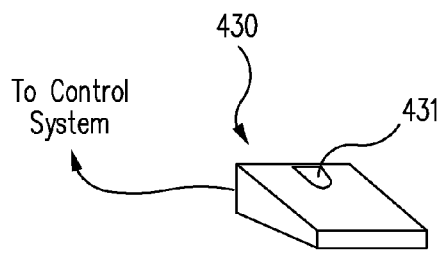
FIG. 4C illustrates an aspect of a foot tray in the patient-side surgeon interface.

In another example, forearm/elbow support 180B is mounted on a movable platform such as saddle stool 410. As shown in FIG. 4B, saddle stool 410 includes a plurality of casters 415 to facilitate movement. One saddle stool with such a support is available as a Salli Saddle Stool with Elbow Rest from Back Designs, Inc. of Novato, Calif., USA. The use of a saddle stool is illustrative only of a movable platform and is not intended to be limiting to this specific stool. In view of this disclosure, a suitable forearm/elbow support can be mounted on a variety of movable platforms on which surgeon 101 can comfortably sit or otherwise be supported.

Such movable platforms allow surgeon 101 to perch on that platform and thereby relax body core muscles and preserve ergonomic spinal alignment during work. The movable platform provides a neutral working position for the surgeon's forearms and a physical reference for returning to an ergonomic pose in master clutch mode. This physical reference reduces cognitive load when using master clutch mode and helps to preserve ergonomic posture.

Control System

Figure 7:
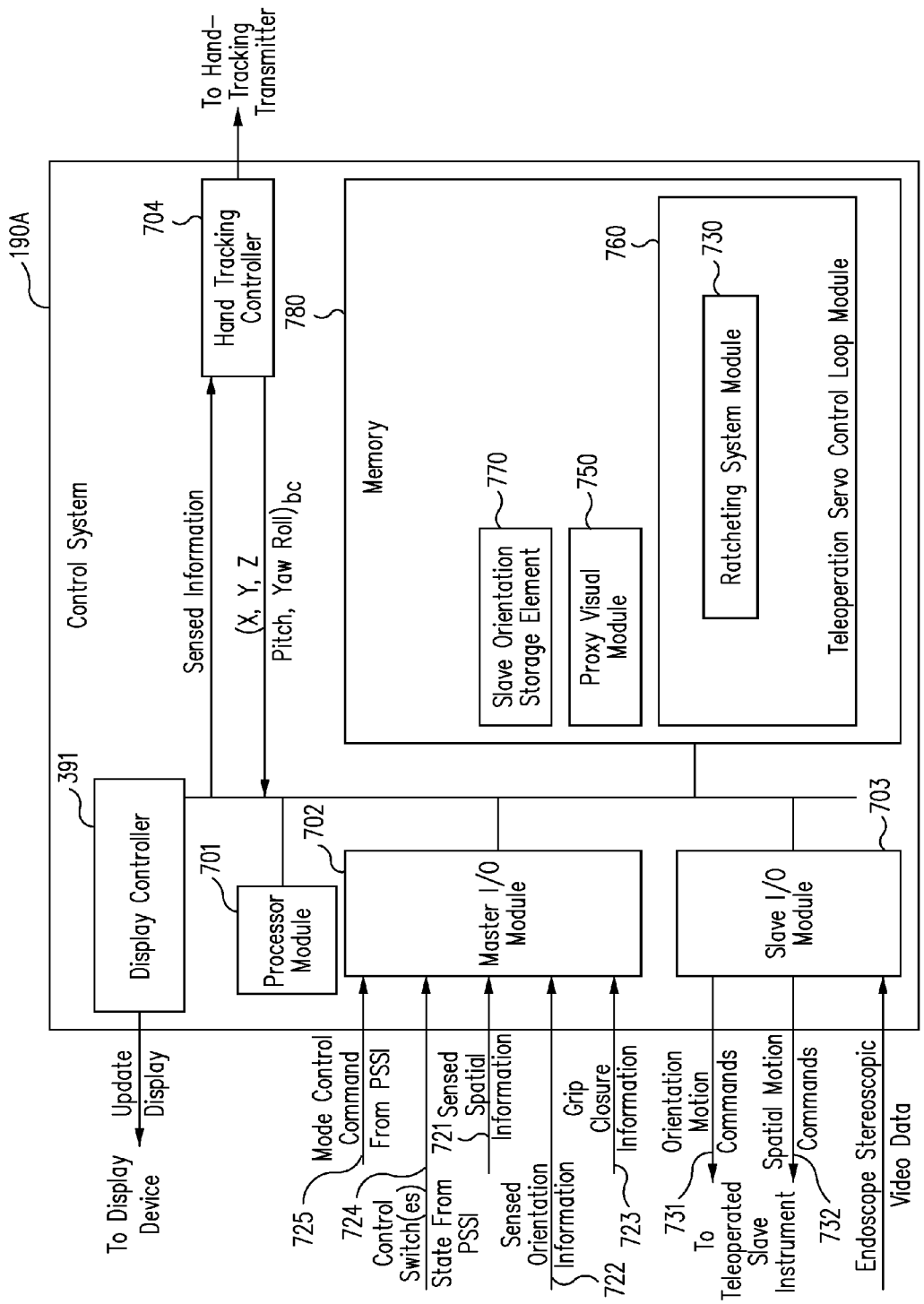
FIG. 7 is a block diagram of a control system that includes modules used to implement various aspects of the control system.

As described above, control system 190, 190A (FIGS. 1A, 1B, 3A, and 7) performs a variety of functions. Control system 190A (FIG. 7) receives both information that is associated with operating in one of the operating modes and information that indicates a mode in which to operate. For example, using master interface input/output module 702, control system 190A receives sensed spatial information 721, sensed orientation information 722, and grip closure information 723 as well as information on the state of control switches 724, e.g., the display and master tool grip presence switches. Control system 190A also receives mode control commands 725 from patient-side surgeon interface (PSSI) 150. The actions taken by control system 190A in response to the state information from the various control switches and the mode control commands were described above and so are not repeated here.

Control system 190A uses a teleoperation servo control system, which executes instructions in a teleoperation servo control loop module 760 on a processor in processor module 701, to translate and to transfer the motion of master tool grip 670 to an associated robotic arm through control commands so that surgeon 601 can effectively manipulate a tip of slave surgical instrument 110. In one aspect, the control commands include orientation motion commands 731 and spatial motion commands 732. The functions performed by the teleoperation servo control system are equivalent to the conventional functions when considered in conjunction with the features described more completely below for control system 190A.

Figure 6A:
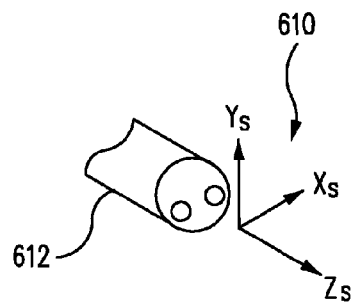
FIG. 6A is illustration of endoscopic coordinate frame utilized in the system of FIGS. 1A and 1B.
Figure 6B:
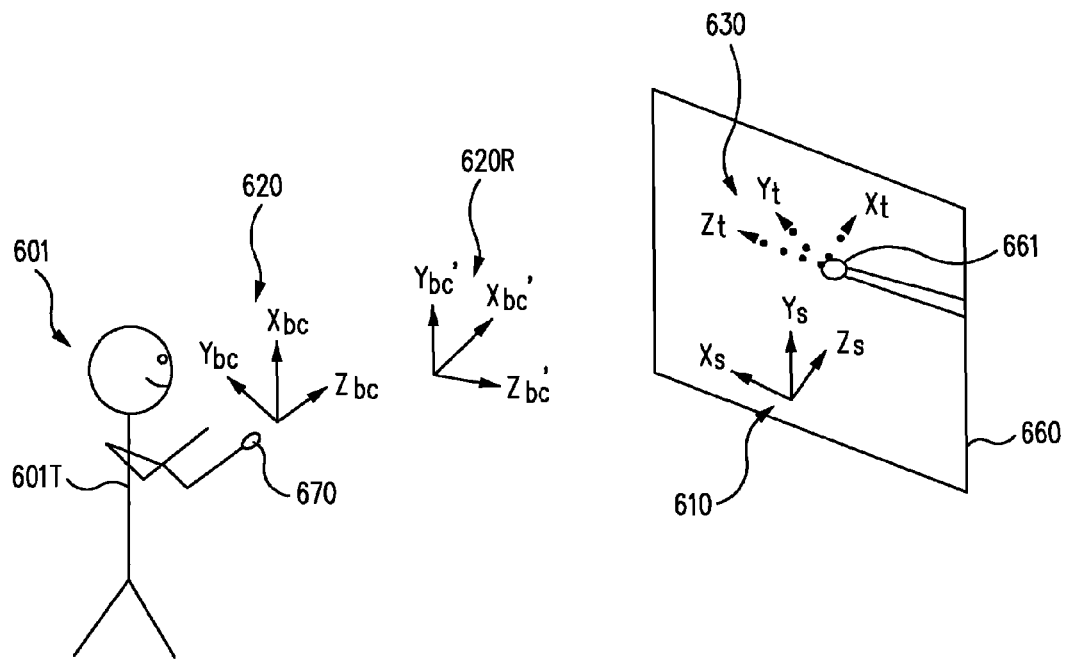
FIG. 6B is illustration of one aspect of a body-centric mapping utilized in the system of FIGS. 1A and 1B.

In FIG. 6A, a conventional endoscopic view coordinate frame 610 for stereoscopic endoscope 612 is illustrated. In FIG. 6B, various coordinate frames 610, 620, and 630 are used in one aspect. As described more completely below, coordinate frames 610, 620, and 630 are used in one aspect of translating motion of master tool grip 670 to motion of a tip of a teleoperated slave surgical instrument.

Control system 190A implements unique mappings and processing in translating sensed spatial information 721, sensed orientation information 722 into orientation motion commands 731 and spatial motion commands 732 to move a tip of a teleoperated slave surgical instrument. In particular, control system 190A, as described more completely below, includes a ratcheting system module 730 that upon execution prevents autonomous or unintentional motion of a slave surgical instrument. Control system 190A can also include a proxy visual module 750, as described more completely below, which is stored in a memory 780 and executed on a processor in processor module 701.

The following description of an implementation of control system 190A is illustrative only and is not intended to be limiting. In view of this description, one knowledgeable in the field can select and implement any desired combination of the described features to accommodate the requirements of a minimally invasive, teleoperated surgical system that includes a patient-side surgeon interface 150.

The combination of the mechanically ungrounded master tool grip 670 in a sterile surgical field and a three-dimensional display device 660 provides a new capability in allowing patient side control of teleoperated slave surgical instruments. As described above, in one aspect, movable three-dimensional display 660 is movable by surgeon 601, who is working in the sterile surgical field. The techniques used to map the motions of master tool grip 670 to movement of a slave surgical instrument end effector 661 as seen in three-dimensional display device 660 by control system 190A are not directly transferrable from the conventional minimally invasive, teleoperated robotic surgical system.

To better understand the problem solved, it is useful to first consider the conventional mapping strategy used by a conventional minimally invasive, teleoperated robotic surgical system with respect to a surgeon's console 114 (FIG. 1B), which is not within the sterile surgical field. The motion mapping strategy for surgeon's console 114 is designed to be both intuitive and ergonomic. To do this, the motion mapping takes advantage of vision and hand workspace collocation. See example, U.S. Pat. No. 7,155,315 (filed Dec. 12, 2005; disclosing "Camera Referenced Control in a Minimally Invasive Surgical Apparatus"), which is incorporated herein by reference in its entirety.

Surgeon 195 (FIG. 1B) sits at surgeon's console 114 and looks into a stereo viewer to see a three-dimensional image from stereoscopic endoscopic 112. The three-dimensional image is presented to surgeon 195 in an immersive way, so that it appears that surgeon 195 is seeing the surgical field directly with her/his own eyes. The stereo vision is scaled such that it perceptually matches the surgeon's own hand-eye workspace. Furthermore, the stereo vision is oriented so that the scene extends in depth along the principal look direction of the surgeon's head, where the head is angled downward by sixty degrees.

As a result of this setup, the visual space of the surgeon perceptually overlaps with the space in which the surgeon moves the master tool manipulators. This architecture ultimately gives the impression that the teleoperated slave surgical instruments are the surgeon's own hands.

Thus, the conventional system accommodates an ideal mapping of the hand-eye space for controlling teleoperated slave surgical instruments. As just noted, when looking at the instruments in the endoscopic view, it is common for the surgeon to perceive that the instruments are in fact her/his own hands.

Control System—Body-centric Mapping

As described above, patient-side surgeon interface 150 allows display device 660 to be positioned and oriented in varying ways with respect to surgeon 601. The conventional collocation mapping, described above, dictates that surgeon 601 would have to move her/his hands along the look direction of stereoscopic display 660 to move the instruments along the endoscopic view direction $Z_s$. This approach may be acceptable for a stereoscopic display device such as that illustrated in FIG. 3C, where the surgeon looks down into display device 160B, but is unacceptable for display devices where the surgeon's view is more horizontal.

Additionally, surgeon 601 would have to move her/his hands up and parallel to the display to move the instruments up in direction $Y_s$ in the endoscopic view. However, this can lead to awkward and non-ergonomic motions when display device 660 is not directly in front of surgeon 601. It would be fatiguing for surgeon 601 to have to continually lift the arms to move the hands up and into display device 660.

To overcome these problems associated with trying to use the conventional visual space, a body-centric mapping is applied, which allows surgeon 601 to register movements relative to her/his own posture. In the example of FIG. 6B, a body-centric coordinate frame 610 includes a body-centric z-coordinate axis $Z_{bc}$, a body-centric x-coordinate axis $X_{bc}$, and a body-centric y-coordinate axis $Y_{bc}$.

In FIG. 6B, body-centric z-coordinate axis $Z_{bc}$ is an axis along which motion of master tool grip 670 is away from and towards torso 601T of surgeon 601. Body-centric x-coordinate axis $X_{bc}$ is an axis along which motion of master tool grip 670 is from the left and to the right with respect to torso 601T of surgeon 601. Body-centric y-coordinate axis $Y_{bc}$ is an axis along which motion of master tool grip 670 is up and down with respect to torso 601T of surgeon 601.

In the image on display device 660, endoscopic view z-coordinate axis $Z_s$ is an axis along the endoscopic view direction, which is into and out of the image on display 660. Endoscope view x-coordinate axis $X_s$ is an axis that extends from right to left in the image on display 660. Endoscope view y-coordinate axis $Y_s$ is an axis that extends up and down in the image on display 660. Coordinate frame 610 is illustrated on display 660 for ease of discussion and is not normally included in the image on display 660. In one aspect, the display coordinate frame for the image on display 660 is the same as endoscopic view coordinate frame 610.

Also, in the image on display device 660 is an end effector 661 of a teleoperated slave surgical instrument for which a tip coordinate frame 630 is defined. Tip z-coordinate axis $Z_t$ of end effector 661 is an axis along the longitudinal axis of the image of the teleoperated slave surgical instrument on display 660. Tip x-coordinate axis $X_t$ and tip coordinate axis $Y_t$ define a plane perpendicular to axis $Z_t$.

Note that for convenience the image of slave surgical instrument end effector 661, sometime referred to as slave surgical instrument tip 661, is used in this description, as this is what the surgeon sees moving. The movement of this image corresponds directly to the movement of the teleoperated slave surgical instrument tip itself. One knowledgeable in the field understands that movement of the image is a direct result of movement of the tip itself by the robot arm in response to a control command from control system 190A, as described herein.

Note that control system 190A maps both data in body centric coordinate frame 620 and data in surgical instrument tip coordinate frame 630 to endoscopic view coordinate frame 610, which is sometimes referred to as a common coordinate frame. This mapping is used in translating movement of master tool tracker 660 to movement of surgical instrument tip 661 in the display coordinate frame.

For example, when seated or standing, surgeon 601 may move master tool grip 670 away from her/his torso 601T along body-centric z-coordinate axis $Z_{bc}$. Master tool grip 670, in this aspect, senses the motion in three-dimensional coordinate frame 610 and provides the sensed spatial information 721 and sensed orientation information 722 to control system 190A.

In control system 190, a hand tracking controller 704 receives the sensed information, e.g., either or both of sensed spatial information 721 and sensed orientation information 722, and outputs new spatial position data ($x_{bc}$, $y_{bc}$, $z_{bc}$) and new orientation data (Pitch, Yaw, Roll). In one aspect, hand tracking controller 704 also is coupled to hand-tracking transmitter 175 and controls the field transmitted by transmitter 175.

Spatial position data ($x_{bc}$, $y_{bc}$, $z_{bc}$) and orientation data (Pitch, Yaw, Roll) are mapped to endoscopic view coordinate frame 610. Using the new mapped data and the current position of end effector 661 in endoscope view coordinate frame 610, the information needed to move end effector 661 to the new position in endoscope view coordinate frame 610 is determined. This information is sent in a control command to the slave instrument. In response to the control command, the teleoperated slave surgical instrument moves the tip along the endoscopic view direction to correspond to the motion of master tool grip 670 along body-centric z-coordinate axis $Z_{bc}$. Consequently, slave instrument tip image 661 in display device 660 moves along z-coordinate $Z_s$.

Similarly, moving master tool grip 670 up along body-centric y-coordinate axis $Y_{bc}$ moves the slave instrument so that slave instrument tip image 661 in display device 660 moves up along endoscope view y-coordinate axis $Y_s$, i.e., the image moves up on display device 660. Moving master tool grip 670 left along body-centric x-coordinate axis $X_{bc}$ moves the slave instrument so that slave instrument tip image 661 in display device 660 moves left across the display along endoscope view x-coordinate axis $X_s$.

This mapping strategy relaxes the assumption that the head, body and arms of surgeon 601 are all aligned with the display coordinate frame. The orientation of the body-centric coordinate frame can be directly managed by surgeon 601. This allows surgeon 601 to manage both ergonomics of the mapping as well as accommodate more flexibility in the arrangement of the surgeon, patient, endoscope and endoscopic display.

One option is to allow surgeon to orient transmitter 175 used by the hand tracking system, e.g., to rotate transmitter 175 using turntable 331 (FIG. 3B). Another related option is to attach a lightweight transmitter 175 in a wearable fashion to the surgeon, so that measured motions are always relative to the surgeon's torso. An alternative is to allow the surgeon to make a pointing or motion gesture to define the orientation frame.

A magnetic hand tracking controller, sensors for use in the master tool grip, and a hand-tracking transmitter suitable for use in one embodiment of this invention are available from Ascension Technology Corporation of Burlington, Vt., USA as a 3D guidance trakSTAR™ System with a Mid-Range Transmitter. (trakSTAR™ is a trademark of Ascension Technology Corporation.). The transmitter generates pulsed DC magnetic fields for high accuracy tracking over medium ranges, which is specified as 78 centimeters (31 inches.) This system provides dynamic tracking with 240 to 420 updates/second for each sensor. The miniaturized passive sensor outputs are unaffected by power-line noise sources. A clear line-of-sight between the transmitter and sensors is not required. There is all attitude tracking and no inertial drift or optical interference. There is high metal immunity and no distortion from non magnetic metals.

Control System—Ergonomic Wrist Orientation Mapping

Figure 5A:
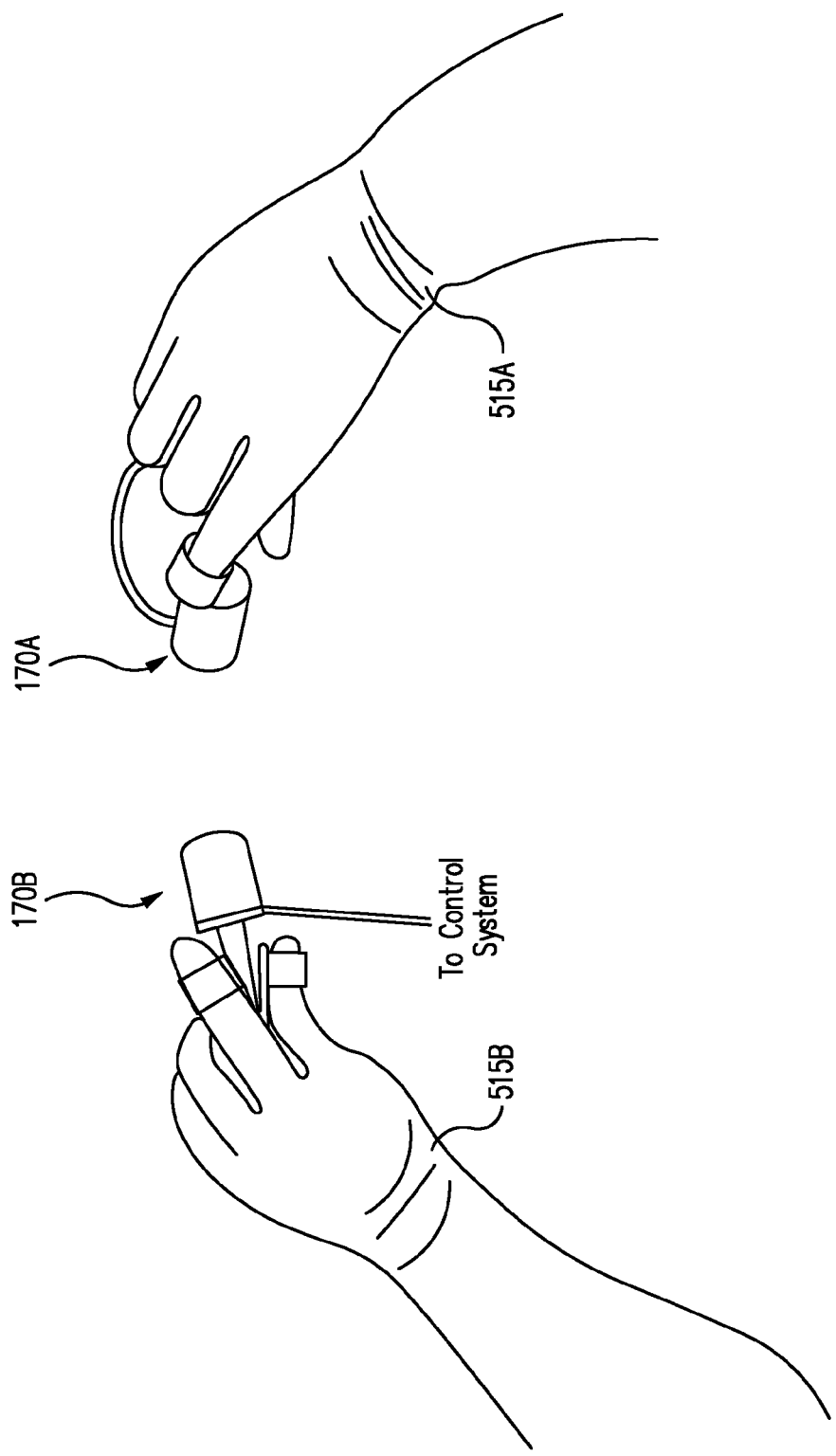
FIG. 5A is an illustration of the wrist orientation that would be required if the display device were oriented vertically so as to reproduce the conventional configuration between the three-dimensional image and the master tool grips.
Figure 5B:
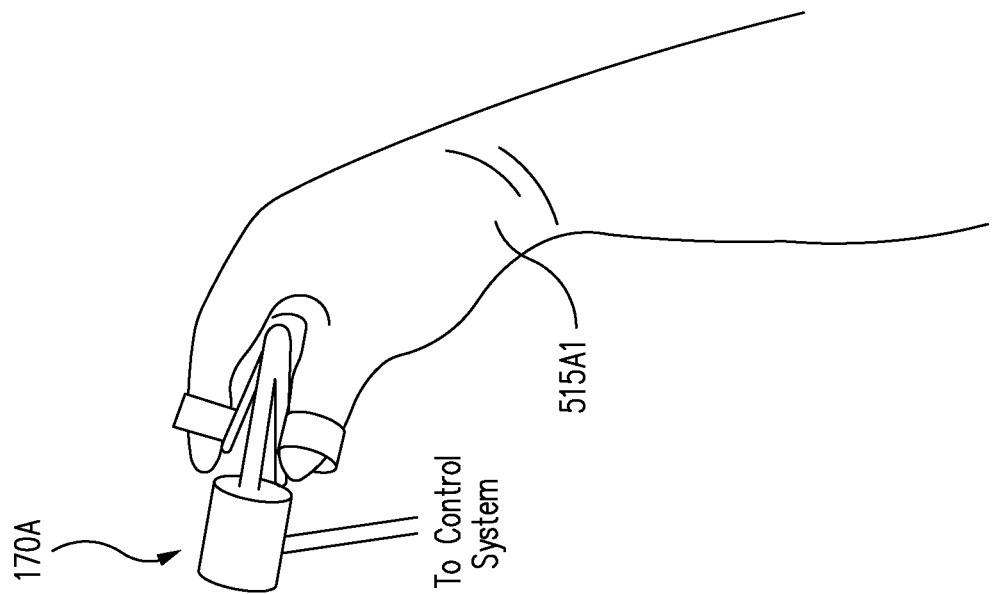
FIG. 5B is an illustration of an improved wrist orientation obtained by utilizing a fixed rotational offset in mapping wrist orientation motions.
Figure 5B:
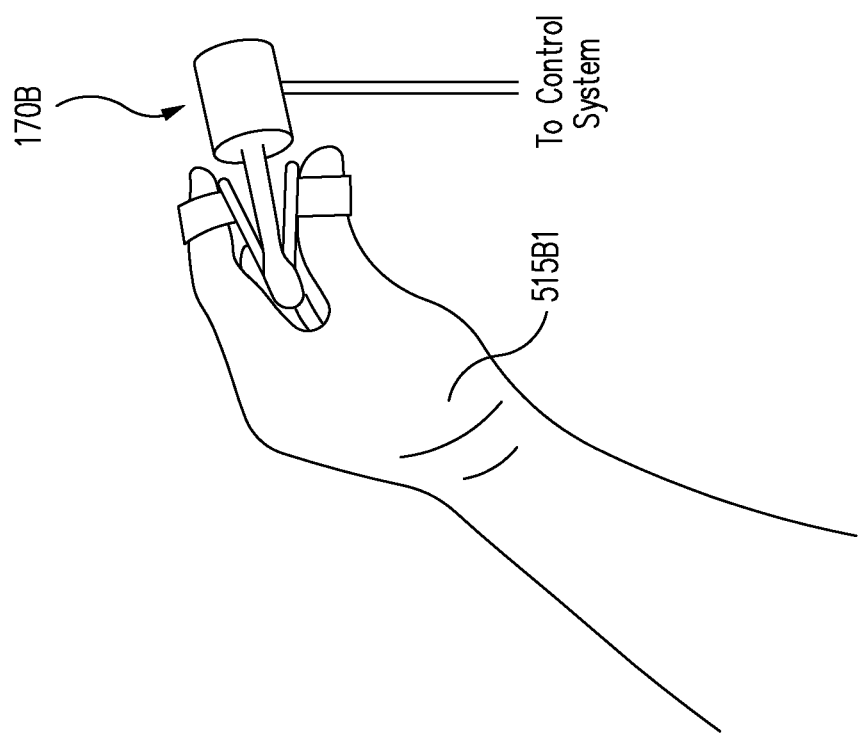

With patient-side surgeon interface 150, display device 160 is not always angled downward by sixty degrees like the console stereo viewer. If display device 160 were oriented too vertically, (i.e., the surgeon's view is normal to the display screen and essentially horizontal) to reproduce the conventional configuration between the three-dimensional image and the master tool grips, surgeon 101 would need to bend her/his wrists 515A, 515B backward into an uncomfortable pose as depicted in FIG. 5A, or otherwise hold the forearms in an uncomfortable pose. While it is possible to operate the slave surgical instruments in such a position, surgeon 101 would find the unnatural position ergonomically undesirable.

Consequently, in one aspect, a fixed rotational offset is used for mapping wrist orientation motions in the body-centric coordinate frame. Specifically, the sensed orientation data from master tool grip 170A, 170B that is received by the servo control loop within control system 190A (FIG. 7) is rotated by a fixed offset. This is represented in FIG. 6B by coordinate frame 620R A fixed offset in the range −45 degrees to −30 degrees has been shown to work well at mitigating this ergonomic problem while still preserving intuitive control. The improved ergonomic pose 515A1, 515B1 permitted by used of this fixed rotational offset is illustrated in 5B.

The anthropomorphic nature of this mapping aspect is that the wrist control is no longer mapped in an absolute one-to-one mapping that is based solely on the mechanical and vision components of the system design. The mapping is instead modified to accommodate a more comfortable wrist range of motion of a human user.

Control System—Ratcheting System

A conventional minimally invasive, teleoperated surgical system required the surgeon to wait until the orientation of the master tool grip and the slave surgical instrument end effector were positioned so that the following mode could be entered without causing an abrupt unwanted slave motion. However, in control system 190A, a ratcheting system module 730 (FIG. 7), within teleoperation servo control loop module 760 is activated, e.g., executed on processor module 701, when surgeon 101 starts to move master tool grip 170. Ratcheting system module 730 as well as module 760 are stored in memory 780. Irrespective of the orientation error between master tool grip 170 and the end-effector of slave surgical instrument 110, the teleoperation servo control loop system enters the following mode between master tool grip 170 and the surgical instrument end effector, sometimes called a slave surgical instrument tip 661.

Ratcheting system module 730 seamlessly and continuously improves the orientation of master tool grip 170 with respect to the slave surgical instrument tip, as master tool grip 170 is moved. Ratcheting system module 730 ratchets the orientation of the slave surgical instrument tip to continuously and seamlessly reduce any orientation error between the slave surgical instrument tip and master tool grip 170. Master tool grip movements that are towards the slave orientation are used to improve the master/slave mapping, but master tool grip movements that are away from the slave orientation are not, and so the master/slave alignment is continually ratcheted towards a proper intuitive relationship that the surgeon can experience. Execution of ratcheting system module 730 achieves the orientation alignment without autonomous motion of either master tool grip 170, or the slave surgical instrument tip.

Execution of ratcheting system module 730 results in intuitive orientation alignment between master tool grip 170 and the slave surgical instrument tip as viewed by surgeon 101 in display device 160. Also, ratcheting system module 730 provides a direct association between what surgeon 101 is doing (manipulating master tool grip 170) and what surgeon 101 is seeing on display device 160 (movement of the slave surgical instrument tip in display device 160). One example of such ratcheting is described in more detail in copending and commonly assigned U.S. patent application Ser. No. 12/495,213 (filed Jun. 30, 2009; disclosing "Ratcheting for Master Alignment of a Teleoperated Minimally-Invasive Surgical Instrument"), which is incorporated herein by reference in its entirety.

Control System—Proxy Visual System

As described above, proxy visuals can be used by a surgeon to proctor another surgeon. In this example, surgeon 195 (FIG. 1B) is proctored by surgeon 101 using patient side surgeon interface 150. However, this configuration is illustrative only. For example, surgeon 101 could use master tool grip 170A (FIG. 2) to control a proxy visual, while surgeon 195 uses master tool grip 170B to control teleoperated slave surgical instrument 110. Any master tool grip can be assigned to a proxy visual and a surgeon can use that master tool grip to proctor another surgeon using a different master tool grip. Patient side surgeon interface 150 facilitates such proctoring without requiring a second surgeon's console, or even a first surgeon's console.

To facilitate proctoring, a proxy visual module 750 is processed as part of the vision processing subsystem in one aspect. The module receives the position and orientation of the master tool grips and renders stereo images, which are composited with the endoscopic camera images in real time and displayed on the surgeon console, assistant display, and patient-side surgeon interface display 160. When surgeon 101 initiates proctoring by taking a predefined action, a proxy visual system loop is activated, e.g., module 750 is executed on processor module 701. The particular action used as the predefined action is not essential so long as control system 190A is configured to recognize that action.

Figure 8:
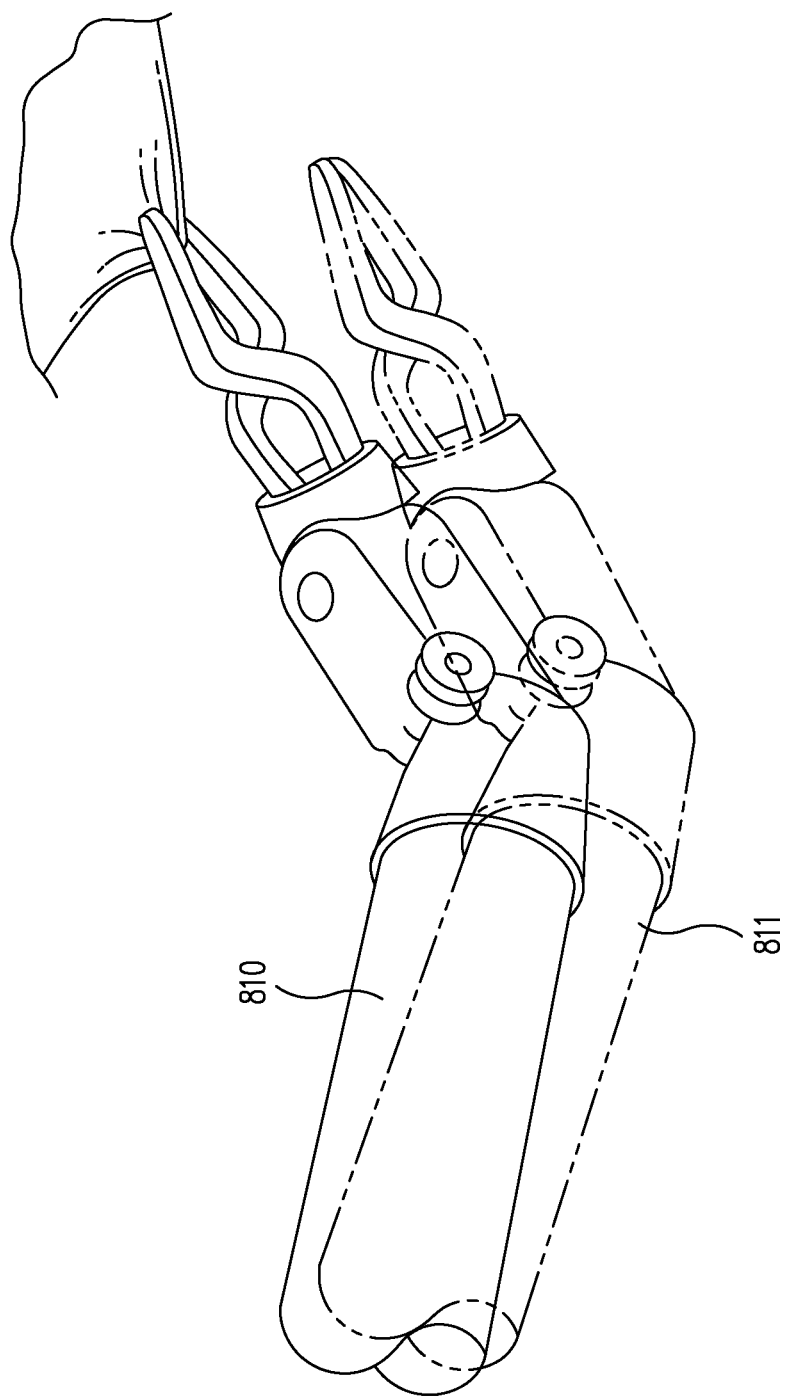
FIG. 8 is an illustration an image, presented on a display device, of a teleoperated slave surgical instrument and a proxy visual, which in this example is a virtual ghost instrument.

In one aspect, the proxy visual is a virtual ghost instrument 811 (FIG. 8) controlled by master tool grip 170, while teleoperated slave surgical instrument 810 is controlled by one of the master tool manipulators of surgeon's console 114. Surgeon 101 sees both instruments 810 and 811 in display device 160, while surgeon 195 sees both instrument 810 and 811 in the stereoscopic display in surgeon's console 114. The use of virtual ghost instrument 811 as a proxy visual is illustrative only and is not intended to be limiting to this particular image. In view of this disclosure, other images can be used for the proxy visual, which facilitate differentiation between the image representing the proxy visual and the image of the actual end effector of the teleoperated slave surgical instrument.

Virtual ghost instrument 811 appears similar to actual instrument 810, except virtual ghost instrument 811 is displayed in a way that clearly distinguishes virtual ghost instrument 811 from actual instrument 810 (e.g., a transparent or translucent ghost-like image, a distinctly colored image, etc.). The control and operation of virtual ghost instrument 811 is the same as that described above for an actual teleoperated surgical instrument. Thus, surgeon 101 can manipulate virtual ghost instrument 811 using master tool grip 170 to demonstrate the proper use of teleoperated slave surgical instrument 810. Surgeon 195 can mimic the motion of virtual ghost instrument 811 with instrument 810.

Virtual ghost instruments are described more completely in commonly assigned United States Patent Application Publication No. US 2009/0192523 A1 (filed Mar. 31, 2009; disclosing "Synthetic Representation of a Surgical Instrument"), which is incorporated herein by reference in its entirety.

Control System—Process flow

Figure 9:
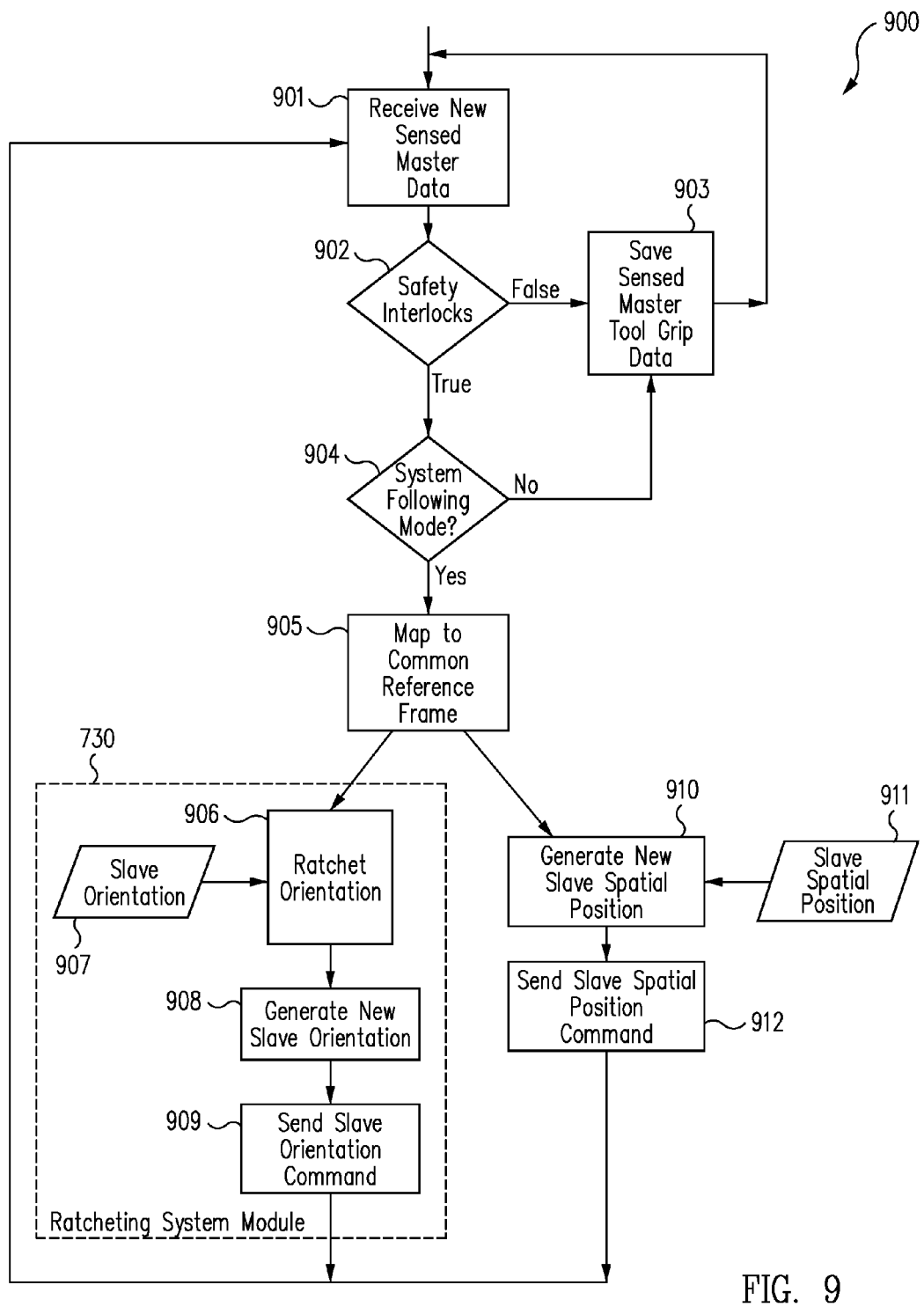
FIG. 9 is a process flow diagram for one aspect of the control system.

FIG. 9 is a process flow diagram for one aspect of a method 900 implemented in a control system 190, 190A in a minimally invasive surgical system 100 including a movable display device 160, a master tool grip 170, a hand-tracking transmitter 175, and a teleoperated slave surgical instrument 110. In RECEIVE NEW SENSED MASTER MOTION DATA operation 901, new sensed spatial data, new sensed orientation data, or both are received by control system 190. Operation 901 transfers processing to safety interlocks check operation 902.

SAFETY INTERLOCKS check operation 902 determines whether the states of the safety interlocks indicate that a following mode operation between at least one master tool grip and a slave surgical instrument is permitted. In addition to the various interlocks described above, another safety interlock is that the surgeon must orient the master grip to roughly match the perceived orientation of the instrument tip to be controlled before initiating the following mode. A total orientation misalignment tolerance of 45 degrees has been found to work well. This tolerance setting is loose enough for the surgeon to reliably match while still resulting in intuitive alignment when following initiates. Residual misalignment is reduced while in following using ratcheting system module 730. Grip closure must also be matched within a tolerance between the master and the slave instrument tip before entering the following mode.

If for example, any one of the presence switches, described above, indicates no presence, an indication is received that display device 160 has been moved, or perhaps the following mode interlocks are not true, safety interlocks check operation 902 is false, which means that following mode is not permissible. Thus, check operation 902 transfers to SAVE SENSED MASTER TOOL GRIP DATA operation 903, which saves the received new data and processing returns to operation 901, in this example.

If the states of the safety interlocks indicate that system 100 including surgeon 101 is in the state required for following mode operation, SAFETY INTERLOCKS check operation 902 transfers processing to SYSTEM FOLLOWING MODE check operation 904. If system 100 is entering following mode or in following mode, check operation 904 transfers to MAP TO COMMON REFERENCE FRAME operation 905 and otherwise to SAVE SENSED MASTER TOOL GRIP DATA operation 903.

MAP TO COMMON REFERENCE FRAME operation 905 maps the received new sensed data to the common reference frame. For example, if the body-centric coordinate frame is used, the sensed data is in the body-centric coordinate frame is mapped to the endoscopic view coordinate frame as described above. Also, the fixed rotational offset to the body-centric coordinate frame is implemented in operation 905 prior to the mapping in one aspect. In addition, a scale factor of 4:1, in one aspect, is used between motions in body-centric coordinate frame 620 and motion in endoscope view coordinate frame 610.

Upon completion of operation 905, RATCHET operation 906 processes the new orientation data and GENERATE NEW SLAVE SPATIAL POSITION operation 910 processes the new position data. RATCHET operation 906 uses a saved SLAVE ORIENTATION 907, which is a current slave orientation stored in slave orientation storage element 770 in memory 780, and the new orientation data to generate a new relative rotation matrix and then transfers to GENERATE NEW SLAVE ORIENTATION operation 908.

GENERATE NEW SLAVE ORIENTATION operation 908 generates a new slave orientation using new relative rotation matrix and transfers processing to SEND SLAVE ORIENTATION COMMAND operation 909. Using the new slave orientation, operation 909 sends a command including the slave orientation and the commanded angular velocity, in the common frame of reference, via slave input/output (I/O) module 703, which results in the slave surgical instrument tip being moved as directed by that command. Upon completion operation 909, in this example, returns to operation 901.

When surgeon 101 moves master tool grip 170 in a way that reduces the orientation error between master tool grip 170 and the tip of slave surgical instrument 110, the ratchet orientation process uses the reduced orientation error in the following between master tool grip 170 and the tip of slave surgical instrument 110, while accounting for how the surgeon grasped master tool grip 170 and whether a roll joint limit was encountered. Conversely, when surgeon 101 moves master tool grip 170 in a way that increases the orientation error between master tool grip 170 and the tip of slave surgical instrument 110, the ratchet orientation process uses the current orientation error, and not the increased orientation error, in the following mode between master tool grip 170 and the tip of slave surgical instrument tip 110.

Operations 906 to 909 are described more completely in copending and commonly assigned U.S. patent application Ser. No. 12/495,213, which was incorporated herein by reference above.

The ratchet orientation process seamlessly and continuously improves the absolute orientation of master tool grip 170 with respect to the tip of slave surgical instrument 110. The ratchet orientation process achieves the continuous improvement in absolute orientation without autonomous motion of either master tool grip 170 or the tip of slave surgical instrument 110.

Generate New Slave Spatial Position operation 910 uses the new spatial position data of master tool grip 670 in the common coordinate frame from operation 905 and a saved current slave surgical instrument spatial position 911 in the common coordinate frame to determine a new slave spatial position for end effector 661 in the common reference frame. Using the new slave spatial position, SEND SLAVE SPATIAL POSITION COMMAND operation 912 sends a command including the slave spatial position and the commanded velocity, in the common frame of reference, via slave input/output (I/O) module 703, which results in the slave surgical instrument tip being moved as directed by that command.

Although described as a control system 190, 190A it is to be appreciated that control system 190, 190A may be implemented in practice by any combination of hardware, software that is executed on a processor, and firmware. Also, its functions, as described herein, may be performed by one unit, or divided up among different components, each of which may be implemented in turn by any combination of hardware, software that is executed on a processor, and firmware. When divided up among different components, the components may be centralized in one location or distributed across system 100 for distributed processing purposes.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

While memory 780 is illustrated as a unified structure, this should not be interpreted as requiring that all memory is at the same physical location. All or part of the memory can be in a different physical location than a processor. Memory refers to a volatile memory, a non-volatile memory, or any combination of the two.

A processor is coupled to a memory containing instructions executed by the processor. This could be accomplished within a computer system, or alternatively via a connection to another computer via modems and analog lines, or digital interfaces and a digital carrier line.

Herein, a computer program product comprises a computer readable medium configured to store computer readable code needed for any part of or all of method 900, or in which computer readable code for any part of or all of method 900 is stored. Some examples of computer program products are CD-ROM discs, DVD discs, flash memory, ROM cards, floppy discs, magnetic tapes, computer hard drives, servers on a network and signals transmitted over a network representing computer readable program code. A tangible computer program product comprises a tangible computer readable medium configured to store computer readable instructions for any part of or all of method 900 or in which computer readable instructions for any part of or all of method 900 is stored. Tangible computer program products are CD-ROM discs, DVD discs, flash memory, ROM cards, floppy discs, magnetic tapes, computer hard drives and other physical storage mediums.

In view of this disclosure, instructions used in any part of or all of method 900 can be implemented in a wide variety of computer system configurations using an operating system and computer programming language of interest to the user.

Further, various different minimally-invasive systems and methods can be implemented in view of this disclosure.

In one a aspect, a minimally-invasive surgical system includes:
a patient-side surgeon interface comprising:
  a) a display device mounted in an operating room; and
  b) a master interface including:
    a mechanically ungrounded master tool grip positioned within the operating room; and
    a hand-tracking transmitter separated and removed from the mechanically ungrounded master tool grip wherein the mechanically ungrounded master tool grip in combination with the hand-tracking transmitter provides sensed position and orientation information in a reference frame associated with a person operating the mechanically ungrounded master tool grip;
  a teleoperated slave surgical instrument comprising a surgical end effector; and
  a control system coupled to the mechanically ungrounded master tool grip, to the hand-tracking transmitter, to the display device and to the teleoperated slave surgical instrument, wherein
    said control system receives the sensed position and orientation information in the reference frame, generates a control command using the sensed position and orientation information, and sends the control command to move the surgical end effector with respect to a reference frame associated with an image displayed on the display device.

This minimally invasive surgical system also includes a manually operated surgical device including a control handle, wherein the control handle is positioned such that the person operating the mechanically ungrounded master tool grip also operates the control handle of the manually operated surgical device.

In another aspect, a method of using this minimally invasive surgical system includes:
  generating sensed position and orientation information by moving a mechanically ungrounded master tool grip, wherein the sensed position and orientation information is in a reference frame associated with a person operating the mechanically ungrounded master tool grip;
  controlling movement of an end effector of a minimally invasive, teleoperated slave surgical instrument based on the sensed position and orientation information.

I claim:

1. A robotic surgical system comprising:
  a patient-side surgeon interface comprising a display device and a master interface,
    wherein the display device is configured to be mounted in an operating room to permit viewing by a person working in a sterile surgical field within the operating room,
    wherein the master interface comprises a mechanically ungrounded master tool grip configured to be positioned within the sterile surgical field and a hand-tracking transmitter configured to be separated and removed from the mechanically ungrounded master tool grip, and
    wherein the mechanically ungrounded master tool grip, in combination with the hand-tracking transmitter, is configured to generate sensed mechanically ungrounded master tool grip position and orientation information in a body-centric reference frame defined with respect to a person operating the mechanically ungrounded master tool grip;
  a teleoperated slave surgical instrument comprising a surgical end effector, wherein at least a portion of the teleoperated slave surgical instrument is configured to be positioned within the sterile surgical field; and
  a control system coupled to the mechanically ungrounded master tool grip, to the hand-tracking transmitter, to the display device, and to the teleoperated slave surgical instrument,
    wherein the control system is configured to receive the sensed position and orientation information in the body-centric reference frame, wherein the control system is configured to generate a control command using the sensed position and orientation information, and wherein the control system is configured to send the control command to move the surgical end effector with respect to a reference frame associated with an image displayed on the display device.

2. The robotic surgical system of claim 1 further comprising:
a manually operated surgical device including a control handle configured to control manual operation of the surgical device by a person, wherein the control handle is configured to be positioned within the sterile surgical field such that the person operating the mechanically ungrounded master tool grip also operates the control handle of the manually operated surgical device to control manual operation of the surgical device.

3. The robotic surgical system of claim 1,
wherein the patient-side surgeon interface further comprises a stereoscopic image viewer configured to be mounted on a boom a fixed distance from the display device in the operating room, and
wherein upon viewing the image on the display device through the stereoscopic image viewer, a stereoscopic image is seen.

4. The robotic surgical system of claim 1,
wherein the patient-side surgeon interface further comprises a display device motion interlock, and
wherein the display device motion interlock is configured to prevent movement of the display device upon receiving a signal from the control system indicating motion of the slave surgical instrument is following motion of the master tool grip.

5. The robotic surgical system of claim 1,
wherein the patient-side surgeon interface further comprises a display device-based presence interlock, and
wherein the display device-based presence interlock is configured to provide a signal to the control system indicating presence or non-presence of a surgeon.

6. The robotic surgical system of claim 1,
wherein the patient-side surgeon interface further comprises a movable boom configured to have the display device mounted thereon, and
wherein the movable boom is configured to permit positioning of the display device about an operating table in the operating room.

7. The robotic surgical system of claim 1,
wherein the patient-side surgeon interface further comprises a stabilization platform configured to be movable with respect to a position of an operating table;
wherein the stabilization platform is configured to support a surgeon's forearms while grasping the master tool grip; and
wherein the stabilization platform is configured to be moved independent from any movement of the display device.

8. The robotic surgical system of claim 7, wherein the stabilization platform includes a plurality of wheels configured to move the stabilization platform with respect to the position of the operating table.

9. The robotic surgical system of claim 7, wherein the movable stabilization platform is configured to be mounted to the operating table.

10. The robotic surgical system of claim 7, wherein the movable stabilization platform is configured to be mounted to a boom.

11. The robotic surgical system of claim 1, wherein the patient-side surgeon interface further comprises a foot tray having at least one pedal coupled to the control system.

12. The robotic surgical system of claim 1, wherein the mechanically ungrounded master tool grip further comprises at least one switch coupled to the control system.

13. The robotic surgical system of claim 12, wherein the at least one switch is configured to provide a signal to the control system indicating presence or non-presence of a surgeon.

14. The robotic surgical system of claim 12, wherein the at least one switch is configured to provide a master clutch signal to the control system.

15. The robotic surgical system of claim 12, wherein the at least one switch is configured to provide a camera control signal to the control system.

16. The robotic surgical system of claim 1, wherein the mechanically ungrounded master tool grip further comprises a grip sensor, wherein the grip sensor is configured to provide grip closure information to the control system, wherein the grip closure information is related to closure of the surgical end effector.

17. The robotic surgical system of claim 1, wherein the control system further comprises a ratcheting system configured to continuously improve an orientation of the master tool grip with respect the surgical end effector as the master tool grip is moved.

18. The robotic surgical system of claim 1 further comprising a surgeon's console coupled to the control system, wherein the surgeon's console includes a stereoscopic display device and a powered master interface.

19. The robotic surgical system of claim 18, wherein the control system further comprises a proxy visual module coupled to the stereoscopic display device of the surgeon's console and coupled to the display device of the patient-side surgeon interface to provide a proxy visual, wherein the proxy visual is moved by moving either of the mechanically ungrounded master tool grip and a master tool manipulator of the surgeon's console.

20. A method comprising:
receiving, by a controller, sensed position and orientation information generated by moving a mechanically ungrounded master tool grip located in a sterile surgical field,
wherein the sensed position and orientation information is in a body-centric reference frame associated with a person, operating the mechanically ungrounded master tool grip within the sterile surgical field; and
controlling, by the controller, movement of an end effector of a minimally invasive teleoperated slave surgical instrument based on the sensed position and orientation information wherein at least a portion of the surgical instrument is in the sterile surgical field.

21. The method of claim 20 further comprising:
controlling manual operation of a manually operated surgical instrument by the person using a control handle of the manually operated surgical instrument, wherein said control handle is within said sterile surgical field.

22. In a robotic surgical system including (a) a patient-side surgeon interface further comprising a display device, a mechanically ungrounded master tool grip, and a hand-tracking transmitter, (b) a teleoperated slave surgical instrument, and (c) a control system, a method comprising:
generating, by the control system, a control command to operate the slave surgical instrument based on movement of the mechanically ungrounded master tool grip;
wherein the patient-side surgeon interface senses position and orientation of the mechanically ungrounded master tool grip in a body-centric reference frame associated with a person operating the mechanically ungrounded master tool grip when the mechanically ungrounded master tool grip is moved in a field of the hand-tracking transmitter and is moved within a sterile surgical field;

wherein the control system receives and uses the sensed position and orientation to generate the control command, with respect to a reference frame associated with an image displayed on the display device; and wherein the control system sends the generated control command to the teleoperated slave surgical instrument.

23. The method of claim 22, further comprising generating, by the control system, a signal to prevent movement of the display device upon the control system entering a following mode between motion of the mechanically ungrounded master tool grip and motion of the teleoperated slave surgical instrument.

24. The method of claim 22, further comprising receiving, by the control system, a signal from a presence switch indicating presence or non-presence of a surgeon.

25. The method of claim 24, wherein the presence switch is included on the mechanically ungrounded master tool grip.

* * * * *